(12) United States Patent
Shimizu et al.

(10) Patent No.: US 10,732,526 B2
(45) Date of Patent: Aug. 4, 2020

(54) ELECTROPHOTOGRAPHIC PHOTOSENSITIVE MEMBER, PROCESS CARTRIDGE, AND IMAGE FORMING APPARATUS

(71) Applicant: KYOCERA Document Solutions Inc., Osaka (JP)

(72) Inventors: Tomofumi Shimizu, Osaka (JP); Keiji Maruo, Osaka (JP); Jun Azuma, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 16/471,154

(22) PCT Filed: Nov. 30, 2017

(86) PCT No.: PCT/JP2017/043015
§ 371 (c)(1),
(2) Date: Jun. 19, 2019

(87) PCT Pub. No.: WO2018/123425
PCT Pub. Date: Jul. 5, 2018

(65) Prior Publication Data
US 2019/0332023 A1    Oct. 31, 2019

(30) Foreign Application Priority Data

Dec. 26, 2016  (JP) .................................. 2016-251080

(51) Int. Cl.
*G03G 5/05*    (2006.01)
*C07D 231/18*    (2006.01)
(Continued)

(52) U.S. Cl.
CPC ........... *G03G 5/056* (2013.01); *C07D 231/18* (2013.01); *C07D 471/04* (2013.01); *C08L 67/03* (2013.01);
(Continued)

(58) Field of Classification Search
CPC ... G03G 5/0564; G03G 5/0609; G03G 5/0614
See application file for complete search history.

(56) References Cited

U.S. PATENT DOCUMENTS

| 8,722,289 B2 * | 5/2014 | Takamura ............ G03G 5/0564 399/159 |
| 2017/0261874 A1 * | 9/2017 | Iwasaki ................ G03G 5/0609 |

FOREIGN PATENT DOCUMENTS

JP    S56-135844 A    10/1981

* cited by examiner

*Primary Examiner* — Peter L Vajda
(74) *Attorney, Agent, or Firm* — Studebaker & Brackett PC

(57) ABSTRACT

An electrophotographic photosensitive member (1) includes a conductive substrate (2) and a photosensitive layer (3). The photosensitive layer (3) is a single-layer photosensitive layer (3c) and contains a charge generating material, a hole transport material, an electron transport material, and a binder resin. The binder resin includes a polyarylate resin represented by general formula (1).

[Formula 1]

(1)

(Continued)

-continued

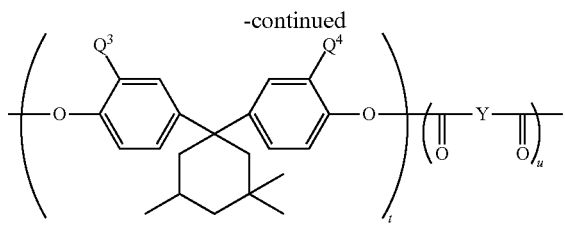

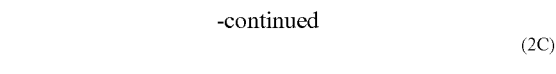

(2C)

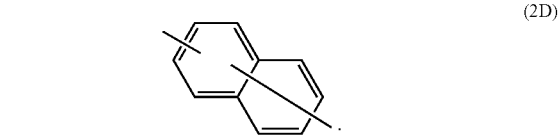

(2D)

In general formula (1), $Q^1$, $Q^2$, $Q^3$, and $Q^4$ each represent a methyl group or a hydrogen atom. r, s, t, and u each represent a number greater than or equal to 15 and less than or equal to 35. X and Y each represent a divalent group represented by chemical formula (2A), chemical formula (2B), chemical formula (2C), or chemical formula (2D), and X and Y are different from each other

15 Claims, 7 Drawing Sheets

[Formula 2]

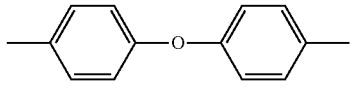

(2A)

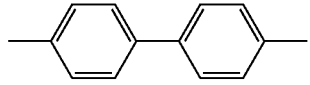

(2B)

(51) Int. Cl.
*C07D 471/04* (2006.01)
*C08L 67/03* (2006.01)
*C09B 47/30* (2006.01)
*G03G 5/06* (2006.01)

(52) U.S. Cl.
CPC ........... *C09B 47/30* (2013.01); *G03G 5/0637* (2013.01); *C08L 2203/20* (2013.01)

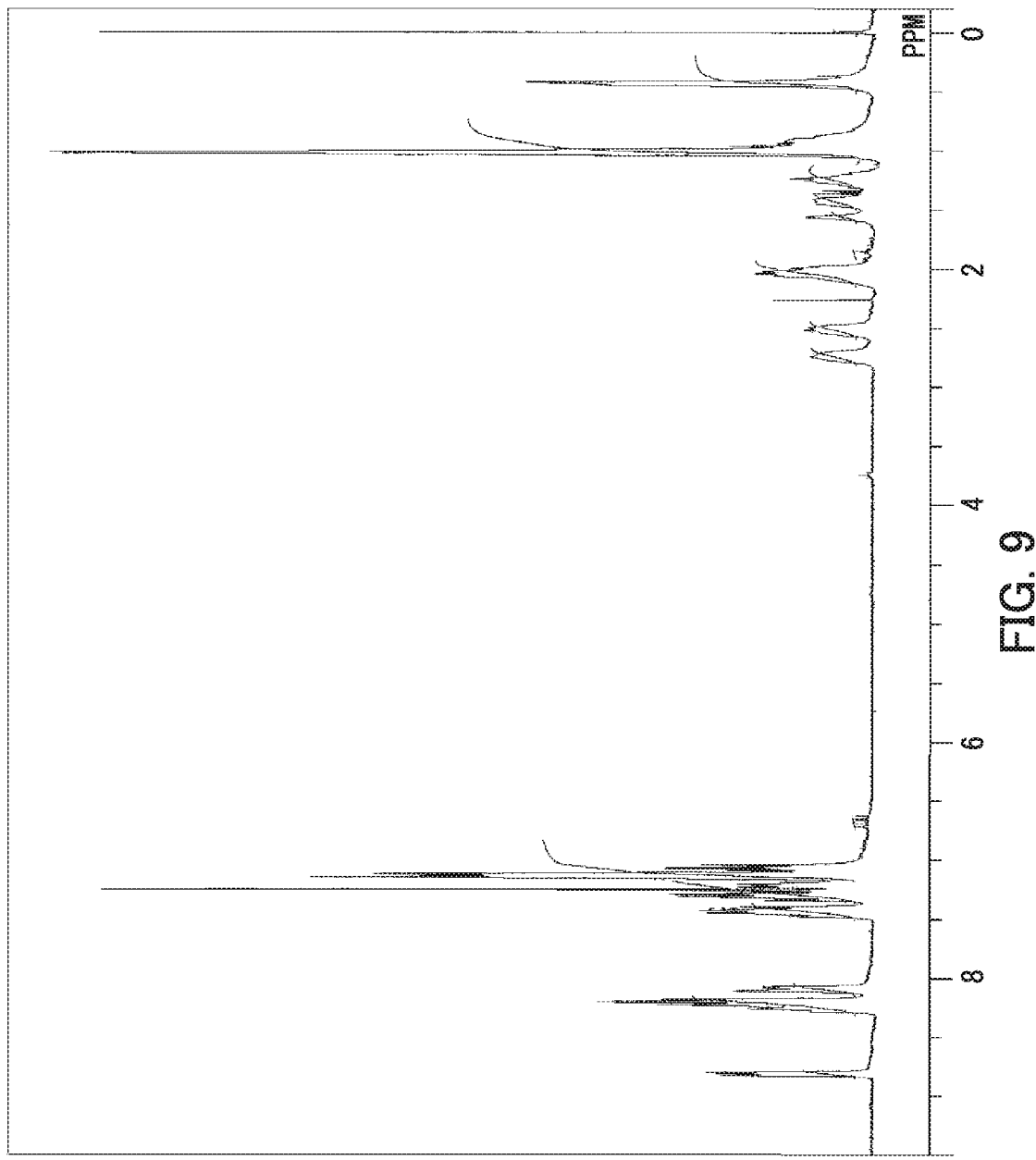

ELECTROPHOTOGRAPHIC PHOTOSENSITIVE MEMBER, PROCESS CARTRIDGE, AND IMAGE FORMING APPARATUS

TECHNICAL FIELD

The present invention relates to an electrophotographic photosensitive member, a process cartridge, and an image forming apparatus.

BACKGROUND ART

Electrophotographic photosensitive members are used as image bearing members of electrophotographic image forming apparatuses (for example, printers and multifunction peripherals). Electrophotographic photosensitive members each include a photosensitive layer. Examples of electrophotographic photosensitive members that are used include single-layer electrophotographic photosensitive members and multi-layer electrophotographic photosensitive members. The single-layer electrophotographic photosensitive members each include a photosensitive layer having a charge generation function and a charge transport function. The multi-layer electrophotographic photosensitive members each include a photosensitive layer including a charge generating layer having a charge generation function and a charge transport layer having a charge transport function.

Patent Literature 1 discloses an electrophotographic photosensitive member containing a specific polyarylate resin.

CITATION LIST

Patent Literature

[Patent Literature 1]
Japanese Patent Application Laid-Open Publication No. 56-135844

SUMMARY OF INVENTION

Technical Problem

However, the present inventors' study has revealed that the electrophotographic photosensitive member containing a polyarylate resin disclosed in Patent Literature 1 is not sufficient to achieve improved anti-fogging performance.

The present invention was made in consideration of the above problem and an object thereof is to provide an electrophotographic photosensitive member including a photosensitive layer that shows excellent anti-fogging performance. Another object of the present invention is to provide a process cartridge and an image forming apparatus that inhibit occurrence of an image defect.

Solution to Problem

An electrophotographic photosensitive member according to the present invention includes a conductive substrate and a photosensitive layer. The photosensitive layer is a single-layer photosensitive layer and contains a charge generating material, a hole transport material, an electron transport material, and a binder resin. The binder resin includes a polyarylate resin. The polyarylate resin is represented by general formula (1) shown below. The electron transport material is represented by general formula (ETM1), general formula (ETM2), general formula (ETM3), general formula (ETM4), or general formula (ETM5) shown below. A scratch resistant depth of the photosensitive layer is no greater than 0.50 μm. A Vickers hardness of the photosensitive layer is at least 17.0 HV.

[Formula 1]

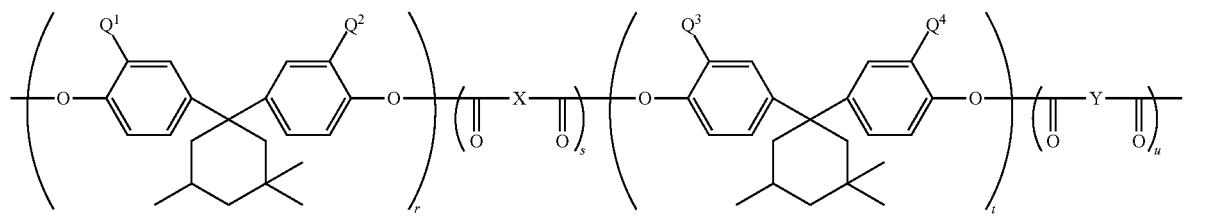

(1)

In general formula (1), $Q^1$, $Q^2$, $Q^3$, and $Q^4$ each represent, independently of one another, a methyl group or a hydrogen atom. r, s, t, and u each represent, independently of one another, a number greater than or equal to 15 and less than or equal to 35. $r+s+t+u=100$. $r+t=s+u$. X and Y each represent, independently of one another, a divalent group represented by chemical formula (2A), chemical formula (2B), chemical formula (2C), or chemical formula (2D) shown below, and X and Y are different from each other.

[Formula 2]

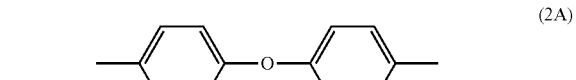

(2A)

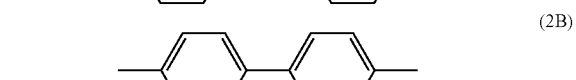

(2B)

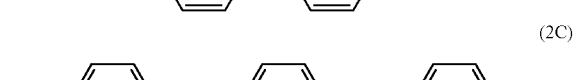

(2C)

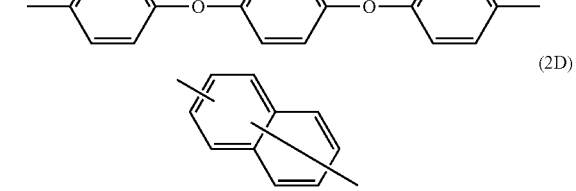

(2D)

[Formula 3]

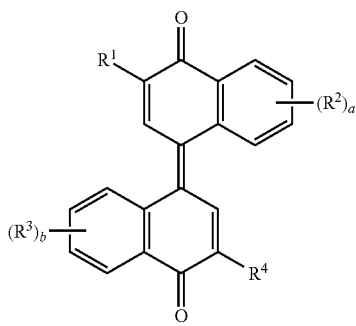

(ETM1)

In general formula (ETM1), $R^1$ and $R^4$ each represent, independently of one another, a hydrogen atom or an alkyl group having a carbon number of at least 1 and no greater than 6. $R^2$ and $R^3$ each represent, independently of one another, an alkyl group having a carbon number of at least 1 and no greater than 6. a and b each represent, independently of one another, an integer of at least 0 and no greater than 4. When a represents an integer of at least 2 and no greater than 4, chemical groups $R^2$ may be the same as or different from one another. When b represents an integer of at least 2 and no greater than 4, chemical groups $R^3$ may be the same as or different from one another.

[Formula 4]

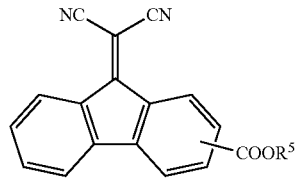

(ETM2)

In general formula (ETM2), $R^5$ represents a hydrogen atom or an alkyl group having a carbon number of at least 1 and no greater than 6 and optionally having a halogen atom.

[Formula 5]

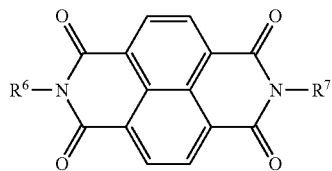

(ETM3)

In general formula (ETM3), $R^6$ and $R^7$ each represent, independently of one another, a hydrogen atom or an aryl group having a carbon number of at least 6 and no greater than 14 and optionally having an alkyl group having a carbon number of at least 1 and no greater than 3.

[Formula 6]

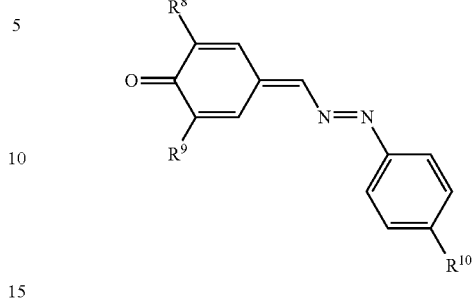

(ETM4)

In general formula (ETM4), $R^8$ and $R^9$ each represent, independently of one another, a hydrogen atom or an alkyl group having a carbon number of at least 1 and no greater than 6, and $R^{10}$ represents a halogen atom or a hydrogen atom

[Formula 7]

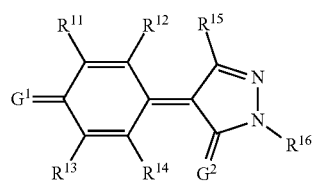

(ETM5)

In general formula (ETM5), $R^{11}$, $R^{12}$, $R^{13}$, $R^{14}$, and $R^{15}$ each represent, independently of one another, a hydrogen atom or an alkyl group having a carbon number of at least 1 and no greater than 6. $R^{16}$ represents a hydrogen atom or an aryl group having a carbon number of at least 6 and no greater than 14 and optionally having a halogen atom. $G^1$ and $G^2$ each represent, independently of one another, an oxygen atom or a sulfur atom.

A process cartridge according to the present invention includes the above-described electrophotographic photosensitive member.

An image forming apparatus according to the present invention includes an image bearing member, a charger, a light exposure section, a development section, and a transfer section. The image bearing member is the above-described electrophotographic photosensitive member. The charger charges a surface of the image bearing member. The charger has a positive charging polarity. The light exposure section exposes the charged surface of the image bearing member to light to form an electrostatic latent image on the surface of the image bearing member. The development section develops the electrostatic latent image into a toner image. The transfer section transfers the toner image from the image bearing member to a transfer target while bringing the transfer target into contact with the surface of the image bearing member.

Advantageous Effects of Invention

The electrophotographic photosensitive member according to the present invention has excellent anti-fogging performance. The process cartridge and the image forming apparatus according to the present invention can inhibit occurrence of an image defect.

BRIEF DESCRIPTION OF DRAWINGS

FIG. 9 is a $^1$H-NMR spectrum of a polyarylate resin represented by chemical formula (R-1).

DESCRIPTION OF EMBODIMENTS

Figure 1:
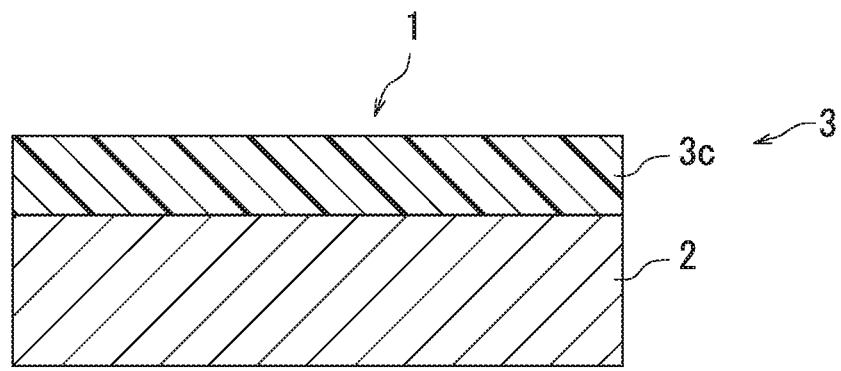
FIG. 1 is a partial cross-sectional view illustrating an example of a structure of an electrophotographic photosensitive member according to a first embodiment of the present invention.

The following describes embodiments of the present invention in detail. However, the present invention is not in any way limited by the following embodiments and appropriate changes may be made when practicing the present invention so long as such changes do not deviate from the intended scope of the present invention. Although description is omitted as appropriate in some instances in order to avoid repetition, such omission does not limit the essence of the present invention. In the present description, the term "-based" may be appended to the name of a chemical compound in order to form a generic name encompassing both the chemical compound itself and derivatives thereof. When the term "-based" is appended to the name of a chemical compound used in the name of a polymer, the term indicates that a repeating unit of the polymer originates from the chemical compound or a derivative thereof.

Hereinafter, an alkyl group having a carbon number of at least 1 and no greater than 6, an alkyl group having a carbon number of at least 1 and no greater than 3, an aryl group having a carbon number of at least 6 and no greater than 14, and a halogen atom each refer to the following.

An alkyl group having a carbon number of at least 1 and no greater than 6 as used herein refers to an unsubstituted straight chain or branched chain alkyl group. Examples of the alkyl group having a carbon number of at least 1 and no greater than 6 include a methyl group, an ethyl group, a propyl group, an isopropyl group, an n-butyl group, an s-butyl group, a t-butyl group, a pentyl group, an isopentyl group, a neopentyl group, and a hexyl group.

An alkyl group having a carbon number of at least 1 and no greater than 3 as used herein refers to an unsubstituted straight chain or branched chain alkyl group. Examples of the alkyl group having a carbon number of at least 1 and no greater than 3 include a methyl group, an ethyl group, a propyl group, an isopropyl group.

An aryl group having a carbon number of at least 6 and no greater than 14 as used herein refers to an unsubstituted aryl group. Examples of the aryl group having a carbon number of at least 6 and no greater than 14 include an unsubstituted monocyclic aromatic hydrocarbon group having a carbon number of at least 6 and no greater than 14, an unsubstituted condensed bicyclic aromatic hydrocarbon group having a carbon number of at least 6 and no greater than 14, and an unsubstituted condensed tricyclic aromatic hydrocarbon group having a carbon number of at least 6 and no greater than 14. More specific examples of the aryl group having a carbon number of at least 6 and no greater than 14 include a phenyl group, a naphthyl group, an anthryl group, and a phenanthryl group.

A halogen atom is for example a fluorine atom, a chlorine atom, a bromine atom, or an iodine atom.

Hereinafter, a functional group "optionally having a halogen atom" means that some or all of hydrogen atoms of the functional group may each be replaced with a halogen atom. A similar concept applies to a functional group "optionally having an alkyl group having a carbon number of at least 1 and no greater than 3".

First Embodiment: Electrophotographic Photosensitive Member

Figure 2:
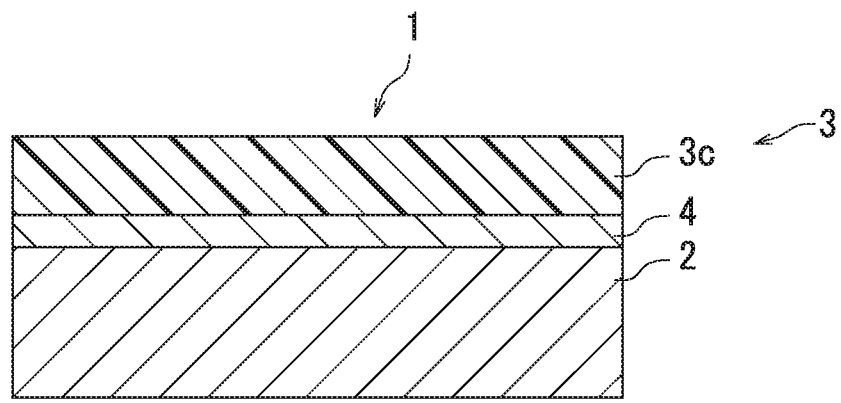
FIG. 2 is a partial cross-sectional view illustrating an example of the structure of the electrophotographic photosensitive member according to the first embodiment of the present invention.
Figure 3:
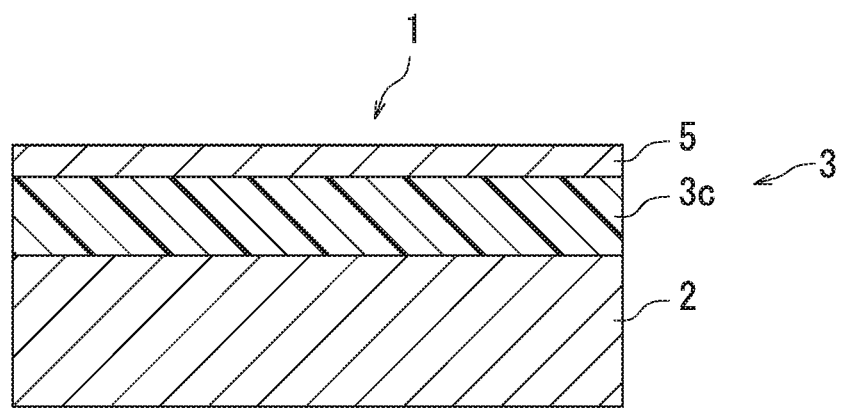
FIG. 3 is a partial cross-sectional view illustrating an example of the structure of the electrophotographic photosensitive member according to the first embodiment of the present invention.

The following describes a structure of an electrophotographic photosensitive member (also referred to below as a photosensitive member) according to a first embodiment of the present invention. FIGS. 1, 2, and 3 are each a partial cross-sectional view illustrating a structure of a photosensitive member 1, which is an example of the first embodiment. As illustrated in FIG. 1, the photosensitive member 1 includes a conductive substrate 2 and a photosensitive layer 3. The photosensitive layer 3 is a single-layer photosensitive layer 3c. The photosensitive layer 3 may be disposed directly on the conductive substrate 2 as illustrated in FIG. 1. Alternatively, the photosensitive member 1 may for example include the conductive substrate 2, an intermediate layer 4 (for example, an undercoat layer), and the photosensitive layer 3 as illustrated in FIG. 2. In the example illustrated in FIG. 2, the photosensitive layer 3 is disposed indirectly on the conductive substrate 2 with the intermediate layer 4 therebetween. Alternatively, the photosensitive member 1 may include a protective layer 5 as an outermost layer as illustrated in FIG. 3.

The following describes elements of the photosensitive member 1 (the conductive substrate 2, the photosensitive layer 3, and the intermediate layer 4). The following further describes a method for producing the photosensitive member 1.

[1. Conductive Substrate]

No particular limitations are placed on the conductive substrate 2 so long as the conductive substrate 2 can be used as a conductive substrate of the photosensitive member 1. A conductive substrate of which at least a surface portion thereof is made from a material having conductivity can be used as the conductive substrate 2. Examples of the conductive substrate 2 include a conductive substrate made from a material having conductivity (a conductive material) and a conductive substrate having a conductive material coating. Examples of conductive materials include aluminum, iron, copper, tin, platinum, silver, vanadium, molybdenum, chromium, cadmium, titanium, nickel, palladium, and indium. Any one of the conductive materials listed above may be used independently, or any two or more of the conductive materials listed above may be used in combination. Examples of combinations of two or more conductive materials include alloys (specific examples include aluminum alloy, stainless steel, and brass). Of the conductive materials listed above, aluminum and an aluminum alloy are preferable in terms of favorable charge mobility from the photosensitive layer 3 to the conductive substrate 2.

The shape of the conductive substrate 2 can be selected as appropriate in accordance with the structure of an image forming apparatus in which the conductive substrate 2 is to be used. The conductive substrate 2 is for example a sheet-shaped conductive substrate or a drum-shaped conductive substrate. The thickness of the conductive substrate 2 can be selected as appropriate in accordance with the shape of the conductive substrate 2.

[2. Photosensitive Layer]

The photosensitive layer 3 contains a charge generating material, a hole transport material, an electron transport material, and a binder resin. The photosensitive layer 3 may further contain an additive. No particular limitations are placed on the thickness of the photosensitive layer 3 so long as the thickness thereof is sufficient to enable the photosensitive layer 3 to function as a photosensitive layer. Specifically, the photosensitive layer 3 may have a thickness of at least 5 µm and no greater than 100 µm, and preferably have a thickness of at least 10 µm and no greater than 50 µm.

The Vickers hardness of the photosensitive layer 3 is measured by a method in accordance with Japanese Industrial Standard (JIS) Z2244. The Vickers hardness is measured using a hardness tester (for example, "MICRO VICKERS HARDNESS TESTER model DMH-1", product of Matsuzawa Co., Ltd). The Vickers hardness can for example be measured under the following conditions: a temperature of 23° C., a diamond indenter load (test force) of 10 gf, a time to reach the test force of 5 seconds, a diamond indenter approach speed of 2 mm/second, and a test force retention time of 1 second.

The photosensitive layer 3 has a Vickers hardness of at least 17.0 HV, preferably at least 18.0 HV in terms of further improving anti-fogging performance, and more preferably at least 19.0 HV. No particular limitations are placed on the upper limit of the Vickers hardness of the photosensitive layer 3 so long as the photosensitive layer 3 is able to sufficiently function as the photosensitive layer of the photosensitive member 1. Preferably, the upper limit of the Vickers hardness of the photosensitive layer 3 is 25.0 HV in terms of manufacturing costs.

Note that the Vickers hardness can for example be controlled by adjusting values of r, s, t, and u in general formula (1) representing a polyarylate resin (1) described below, types of X and Y in general formula (1); and a type and an amount of an electron transport material described below.

A scratch resistant depth (also referred to below as a scratch depth) of the photosensitive layer 3 means a depth of a scratch created by scratching the photosensitive layer 3 under specific conditions described below. The scratch depth is measured through first to fourth steps described below using a scratching apparatus in accordance with JIS K5600-5-5. The scratching apparatus includes a fixture and a scratching stylus. The scratching stylus has a semispherical sapphire tip having a diameter of 1 mm.

In the first step, the photosensitive member 1 is fixed to an upper surface of the fixture with a longitudinal direction of the photosensitive member 1 parallel with a longitudinal direction of the fixture. In the second step, the scratching stylus is brought into vertical contact with a surface of the photosensitive layer 3. In the third step, the fixture and the photosensitive member 1 fixed to the upper surface of the fixture are caused to move by 30 mm at a rate of 30 mm/minute in the longitudinal direction of the fixture while a load of 10 g is applied from the scratching stylus to the photosensitive layer 3. Through the third step, a scratch is created on the surface of the photosensitive layer 3. In the fourth step, the greatest depth of the scratch is measured as a scratch depth.

Through the above, an overview of the measurement method of the scratch depth has been described. The measurement method of the scratch depth will be explained in detail in association with Examples.

The scratch depth of the photosensitive layer 3 is no greater than 0.50 µm. In terms of further improving anti-fogging performance, the scratch depth of the photosensitive layer 3 is preferably no greater than 0.45 µm, and more preferably no greater than 0.42 µm. No particular limitations are placed on the lower limit of the scratch depth of the photosensitive layer 3 so long as the photosensitive layer 3 is able to function as a photosensitive layer of the photosensitive member 1. For example, the lower limit of the scratch depth of the photosensitive layer 3 may be 0.00 µm. However, in terms of manufacturing costs, the lower limit is preferably 0.10 µm.

Note that the scratch depth can for example be controlled by adjusting the values of r, s, t, and u in general formula (1) representing the polyarylate resin (1) described below; the types of X and Y in general formula (1), and the type and the amount of the electron transport material described below.

The following describes a charge generating material, a hole transport material, an electron transport material, a binder resin, and an additive, which is an optional component.

(Charge Generating Material)

No particular limitations are placed on the charge generating material other than being a charge generating material that can be used in the photosensitive member. Examples of charge generating materials include phthalocyanine-based pigments, perylene-based pigments, bisazo pigments, trisazo pigments, dithioketopyrrolopyrrole pigments, metal-free naphthalocyanine pigments, metal naphthalocyanine pigments, squaraine pigments, indigo pigments, azulenium pigments, cyanine pigments, powders of inorganic photoconductive materials (for example, selenium, selenium-tellurium, selenium-arsenic, cadmium sulfide, and amorphous silicon), pyrylium pigments, anthanthrone-based pigments, triphenylmethane-based pigments, threne-based pigments, toluidine-based pigments, pyrazoline-based pigments, and quinacridone-based pigments. One charge generating material may be used independently, or two or more charge generating materials may be used in combination. Examples of phthalocyanine-based pigments include metal-free phthalocyanine and metal phthalocyanine. Examples of metal phthalocyanine include titanyl phthalocyanine, hydroxygallium phthalocyanine, and chlorogallium phthalocyanine. The phthalocyanine-based pigments may be crystalline or non-crystalline. No particular limitations are placed on the crystal structure (for example, α-form, β-form, X-form, Y-form, V-form, and II-form) of the phthalocyanine-based pigments, and phthalocyanine-based pigments having various different crystal structures may be used.

An example of crystalline metal-free phthalocyanine is metal-free phthalocyanine having an X-form crystal structure (also referred to below as X-form metal-free phthalocyanine). Examples of crystalline titanyl phthalocyanine include titanyl phthalocyanines having α-form, β-form, and Y-form crystal structures (also referred to below as α-form titanyl phthalocyanine, β-form titanyl phthalocyanine, and Y-form titanyl phthalocyanine, respectively). An example of crystalline hydroxygallium phthalocyanine is hydroxygallium phthalocyanine having a V-form crystal structure.

In a situation in which the photosensitive member 1 is used in a digital optical system image forming apparatus, it is preferable to use a charge generating material that is sensitive to a range of wavelengths greater than or equal to 700 nm. An example of a charge generating material that is sensitive to a range of wavelengths greater than or equal to 700 nm is a phthalocyanine-based pigment. In particular, X-form metal-free phthalocyanine is preferable in terms of efficient charge generation. The digital optical system image forming apparatus may for example be a laser beam printer or a facsimile machine in which a light source such as a semiconductor laser is used.

In a situation in which the photosensitive member 1 is used in an image forming apparatus that employs a short-wavelength laser light source, it is preferable to use, for example, an anthanthrone-based pigment or a perylene-based pigment as a charge generating material. The wavelength of a short-wavelength laser is for example approximately 350 nm to 550 nm.

Examples of charge generating materials include phthalocyanine-based pigments represented by chemical formulae (CGM-1) to (CGM-4) shown below (also referred to below as charge generating materials (CGM-1) to (CGM-4), respectively).

[Formula 8]

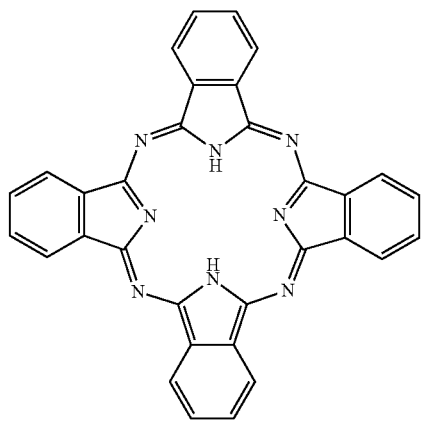

(CGM-1)

[Formula 9]

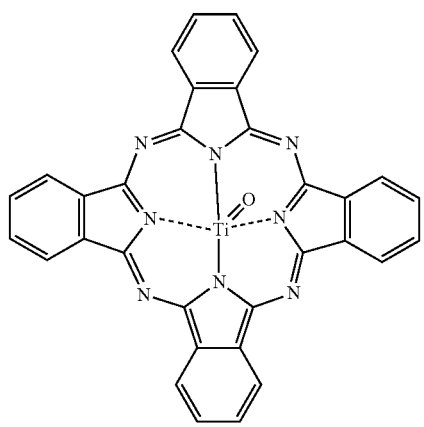

(CGM-2)

[Formula 10]

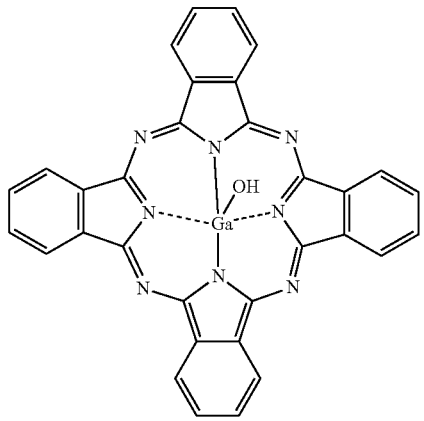

(CGM-3)

[Formula 11]

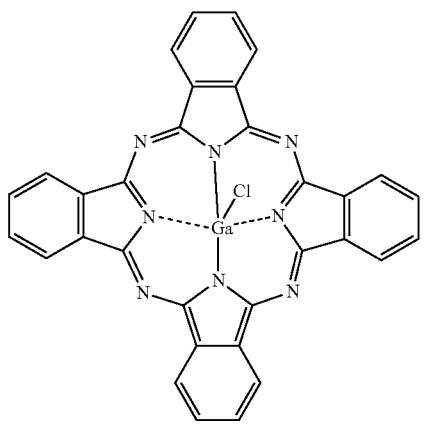

(CGM-4)

In terms of efficient charge generation, the charge generating material is preferably contained in an amount of at least 0.1 parts by mass and no greater than 50 parts by mass relative to 100 parts by mass of the binder resin, more preferably in an amount of at least 0.5 parts by mass and no greater than 30 parts by mass, and particularly preferably in an amount of at least 0.5 parts by mass and no greater than 4.5 parts by mass.

(Hole Transport Material)

Examples of hole transport materials include nitrogen-containing cyclic compounds and condensed polycyclic compounds. Examples of nitrogen-containing cyclic compounds and condensed polycyclic compounds include triphenylamine derivatives, diamine derivatives (specific examples include N,N,N',N'-tetraphenylbenzidine derivatives, N,N,N',N'-tetraphenylphenylenediamine derivatives, N,N,N',N'-tetraphenylnaphtylenediamine derivatives, di(aminophenylethenyl)benzene derivatives, and N,N,N',N'-tetraphenylphenanthrylenediamine derivatives), oxadiazole-based compounds (specific examples include 2,5-di(4-methylaminophenyl)-1,3,4-oxadiazole), styryl-based compounds (specific example include 9-(4-diethylaminostyryl)anthracene), carbazole-based compounds (specific examples include polyvinyl carbazole), organic polysilane compounds, pyrazoline-based compounds (specific examples include 1-phenyl-3-(p-dimethylaminophenyl)pyrazoline), hydrazone-based compounds, indole-based compounds, oxazole-based compounds, isoxazole-based compounds, thiazole-based compounds, thiadiazole-based compounds, imidazole-based compounds, pyrazole-based compounds, and triazole-based compounds. Any one of the hole transport materials listed above may be used independently, or any two or more of the hole transport materials listed above may be used in combination.

Of the hole transport materials listed above, in terms of efficient hole transport, a compound represented by general formula (HTM 1) shown below is preferable, and a compound represented by chemical formula (HTM1-1) shown below (also referred to below as a hole transport material (HTM1-1)) is more preferable.

[Formula 12]

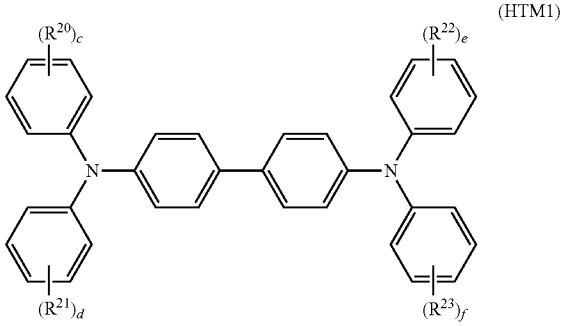

(HTM1)

In general formula (HTM1), $R^{20}$, $R^{21}$, $R^{22}$, and $R^{23}$ each represent, independently of one another, an alkyl group having a carbon number of at least 1 and no greater than 6. c, d, e, and f each represent, independently of one another, an integer of at least 0 and no greater than 5. When c represents an integer of at least 2 and no greater than 5, chemical groups $R^{20}$ may be the same as or different from one another. When d represents an integer of at least 2 and no greater than 5, chemical groups $R^{21}$ may be the same as or different from one another. When e represents an integer of at least 2 and no greater than 5, chemical groups $R^{22}$ may be the same as or different from one another. When f represents an integer of at least 2 and no greater than 5, chemical groups $R^{23}$ may be the same as or different from one another.

[Formula 13]

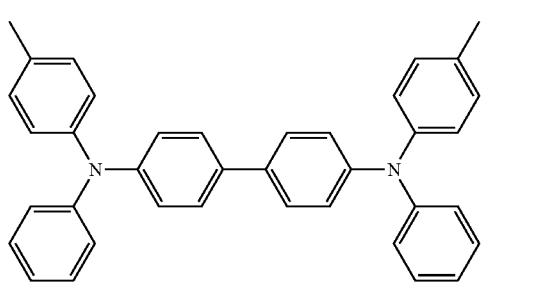

(HTM1-1)

In terms of efficient hole transport, the hole transport material is preferably contained in an amount of at least 10 parts by mass and no greater than 200 parts by mass relative to 100 parts by mass of the binder resin, and more preferably in an amount of at least 10 parts by mass and no greater than 100 parts by mass.

(Electron Transport Material)

The electron transport material is represented by general formula (ETM1), general formula (ETM2), general formula (ETM3), general formula (ETM4), or general formula (ETM5) shown below. These electron transport materials are also referred to below as electron transport materials (ETM1) to (ETM5), respectively. The photosensitive layer 3 may contain only one of these electron transport materials or may contain two or more of the electron transport materials.

[Formula 14]

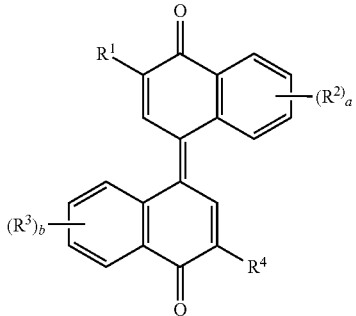

(ETM1)

In general formula (ETM1), $R^1$ and $R^4$ each represent, independently of one another, a hydrogen atom or an alkyl group having a carbon number of at least 1 and no greater than 6. $R^2$ and $R^3$ each represent, independently of one another, an alkyl group having a carbon number of at least 1 and no greater than 6. a and b each represent, independently of one another, an integer of at least 0 and no greater than 4. When a represents an integer of at least 2 and no greater than 4, chemical groups $R^2$ may be the same as or different from one another. When b represents an integer of at least 2 and no greater than 4, chemical groups $R^3$ may be the same as or different from one another.

[Formula 15]

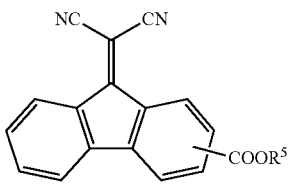

(ETM2)

In general formula (ETM2), $R^5$ represents a hydrogen atom or an alkyl group having a carbon number of at least 1 and no greater than 6 and optionally having a halogen atom.

[Formula 16]

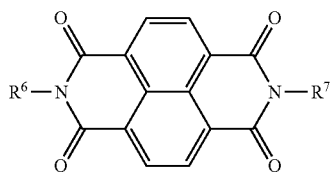

(ETM3)

In general formula (ETM3), $R^6$ and $R^7$ each represent, independently of one another, a hydrogen atom or an aryl group having a carbon number of at least 6 and no greater than 14 and optionally having an alkyl group having a carbon number of at least 1 and no greater than 3.

[Formula 17]

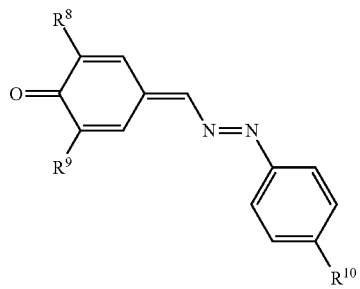

(ETM4)

In general formula (ETM4), $R^8$ and $R^9$ each represent, independently of one another, a hydrogen atom or an alkyl group having a carbon number of at least 1 and no greater than 6. $R^{10}$ represents a halogen atom or a hydrogen atom.

[Formula 18]

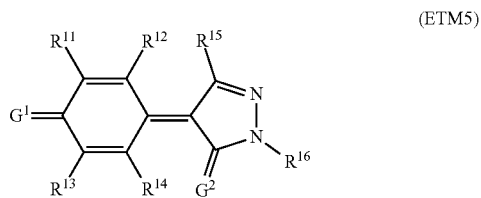

(ETM5)

In general formula (ETM5), $R^{11}$, $R^{12}$, $R^{13}$, $R^{14}$, and $R^{15}$ each represent, independently of one another, a hydrogen atom or an alkyl group having a carbon number of at least 1 and no greater than 6. $R^{16}$ represents a hydrogen atom or an aryl group having a carbon number of at least 6 and no greater than 14 and optionally having a halogen atom. $G^1$ and $G^2$ each represent, independently of one another, an oxygen atom or a sulfur atom.

In terms of further improving anti-fogging performance, preferably, $R^1$ and $R^4$ in general formula (ETM1) each represent, independently of one another, an alkyl group having a carbon number of at least 1 and no greater than 6, and more preferably a branched chain alkyl group having a carbon number of at least 1 and no greater than 6. In terms of further improving anti-fogging performance, preferably, a and b in general formula (ETM1) each represent 0. The electron transport material (ETM1) represented by general formula (ETM1) is for example an electron transport material represented by chemical formula (ETM1-1) shown below (also referred to below as an electron transport material (ETM1-1)).

[Formula 19]

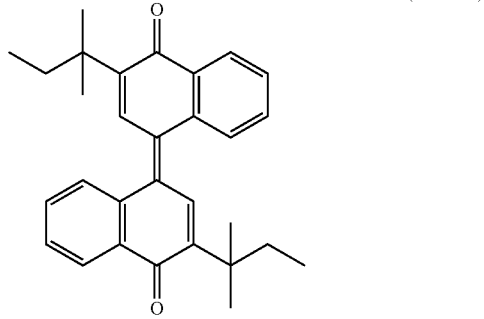

(ETM1-1)

In terms of further improving anti-fogging performance, preferably, $R^5$ in general formula (ETM2) represents an alkyl group having a carbon number of at least 1 and no greater than 6 and optionally having a halogen atom, and more preferably an alkyl group having a carbon number of at least 1 and no greater than 6 and having a chlorine atom. The electron transport material (ETM2) represented by general formula (ETM2) is for example an electron transport material represented by chemical formula (ETM2-1) shown below (also referred to below as an electron transport material (ETM2-1)).

[Formula 20]

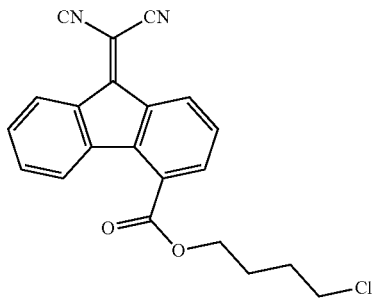

(ETM2-1)

In terms of further improving anti-fogging performance, preferably, $R^6$ and $R^7$ in general formula (ETM3) each represent, independently of one another, an aryl group having a carbon number of at least 6 and no greater than 14 and optionally having an alkyl group having a carbon number of at least 1 and no greater than 3, more preferably a phenyl group optionally having an alkyl group having a carbon number of at least 1 and no greater than 3, and still more preferably a phenyl group having an alkyl group having a carbon number of at least 1 and no greater than 3. The electron transport material (ETM3) represented by general formula (ETM3) is for example an electron transport material represented by chemical formula (ETM3-1) shown below (also referred to below as an electron transport material (ETM3-1)).

[Formula 21]

(ETM3-1)

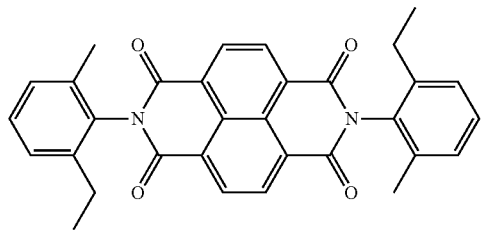

In terms of further improving anti-fogging performance, preferably, $R^8$ and $R^9$ in general formula (ETM4) each represent, independently of one another, an alkyl group having a carbon number of at least 1 and no greater than 6, and more preferably a branched chain alkyl group having a carbon number of at least 1 and no greater than 6. In terms of further improving anti-fogging performance, preferably. $R^{10}$ in general formula (ETM4) represents a halogen atom, and more preferably a chlorine atom. The electron transport material (ETM4) represented by general formula (ETM4) is for example an electron transport material represented by chemical formula (ETM4-1) shown below (also referred to below as an electron transport material (ETM4-1)).

[Formula 22]

(ETM4-1)

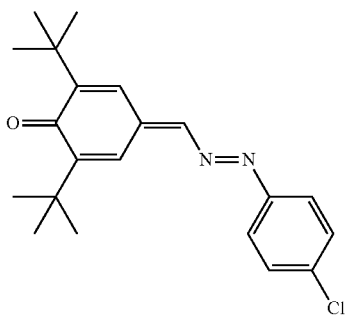

In terms of further improving anti-fogging performance, preferably, $R^{11}$, $R^{13}$, and $R^{15}$ in general formula (ETM5) each represent, independently of one another, an alkyl group having a carbon number of at least 1 and no greater than 6, and more preferably a branched chain alkyl group having a carbon number of at least 1 and no greater than 6. In terms of further improving anti-fogging performance, preferably. $R^{12}$ and $R^{14}$ in general formula (ETM5) each represent a hydrogen atom. In terms of further improving anti-fogging performance, preferably, $R^{16}$ in general formula (ETM5) represents an aryl group having a carbon number of at least 6 and no greater than 14 and optionally having a halogen atom, more preferably a phenyl group optionally having a halogen atom, still more preferably a phenyl group having a chlorine atom, and particularly preferably a phenyl group having a plurality of chlorine atoms. In terms of further improving anti-fogging performance, preferably, $G^1$ and $G^2$ in general formula (ETM5) each represent an oxygen atom. The electron transport material (ETM5) represented by general formula (ETM5) is for example an electron transport material represented by chemical formula (ETM5-1) shown below (also referred to below as an electron transport material (ETM5-1)).

[Formula 23]

(ETM5-1)

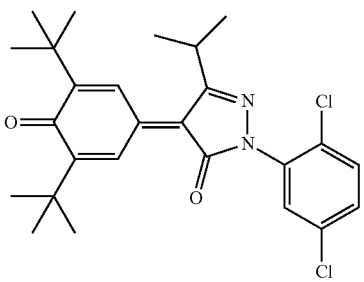

Of the electron transport materials mentioned above, the electron transport material (ETM1), the electron transport material (ETM2), and the electron transport material (ETM5) are preferable in terms of further improving anti-fogging performance, and the electron transport material (ETM1-1), the electron transport material (ETM2-1), and the electron transport material (ETM5-1) are more preferable.

The photosensitive layer 3 may contain an additional electron transport material other than the electron transport materials (ETM1) to (ETM5). Examples of additional electron transport materials that can be used include quinone-based compounds, diimide-based compounds, hydrazone-based compounds, malononitrile-based compounds, thiopyran-based compounds, trinitrothioxanthone-based compounds, 3,4,5,7-tetranitro-9-fluorenone-based compounds, dinitroanthracene-based compounds, dinitroacridine-based compounds, tetracyanoethylene, 2,4,8-trinitro-thioxanthone, dinitrobenzene, dinitroacridine, succinic anhydride, maleic anhydride, and dibromomaleic anhydride that have different structures from the electron transport materials (ETM1) to (ETM5).

In terms of efficient electron transport, the electron transport material is preferably contained in an amount of at least 5 parts by mass and no greater than 100 parts by mass relative to 100 parts by mass of the binder resin, and more preferably in an amount of at least 10 parts by mass and no greater than 80 parts by mass.

(Binder Resin)

The binder resin includes a polyarylate resin represented by general formula (1) shown below (also referred to below as a polyarylate resin (1)).

[Formula 24]

(1)

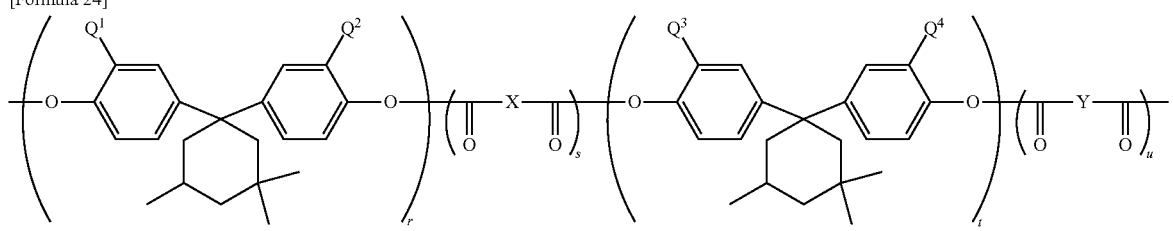

In general formula (1), $Q^1$, $Q^2$, $Q^3$, and $Q^4$ each represent, independently of one another, a methyl group or a hydrogen atom. r, s, t, and u each represent, independently of one another, a number greater than or equal to 15 and less than or equal to 35. $r+s+t+u=100$. $r+t=s+u$. X and Y each represent, independently of one another, a divalent group represented by chemical formula (2A), chemical formula (2B), chemical formula (2C), or chemical formula (2D) shown below. X and Y are different from each other.

[Formula 25]

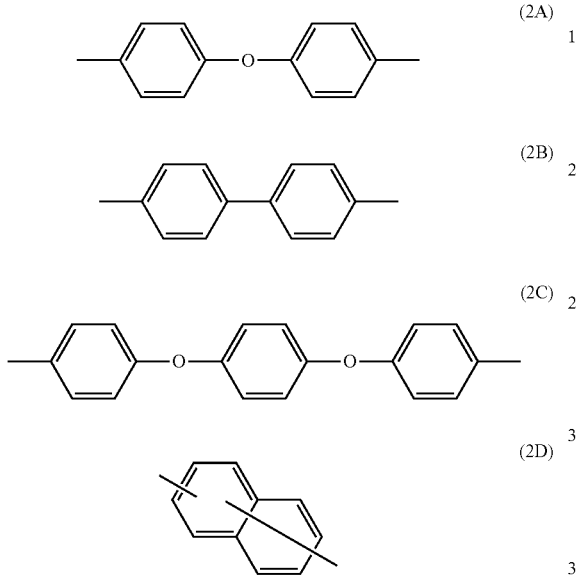

In terms of further improving anti-fogging performance, preferably, X and Y in general formula (1) each represent, independently of one another, a divalent group represented by chemical formula (2A), chemical formula (2B), or chemical formula (2D). In terms of further improving anti-fogging performance, more preferably, X in general formula (1) represents a divalent group represented by chemical formula (2D), and Y represents a divalent group represented by chemical formula (2A) or chemical formula (2B). In terms of further improving anti-fogging performance, preferably, $Q^1$, $Q^2$, $Q^3$, and $Q^4$ in general formula (1) each represent a methyl group.

In terms of further improving anti-fogging performance and improving formability of the photosensitive layer 3, preferably, r, s, t, and u in general formula (1) each represent, independently of one another, a number greater than or equal to 20 and less than or equal to 30.

The polyarylate resin (1) includes a repeating unit represented by general formula (1-1) shown below (also referred to below as a repeating unit (1-1)), a repeating unit represented by general formula (1-2) shown below (also referred to below as a repeating unit (1-2)), a repeating unit represented by general formula (1-3) shown below (also referred to below as a repeating unit (1-3)), and a repeating unit represented by general formula (1-4) shown below (also referred to below as a repeating unit (1-4)).

[Formula 26]

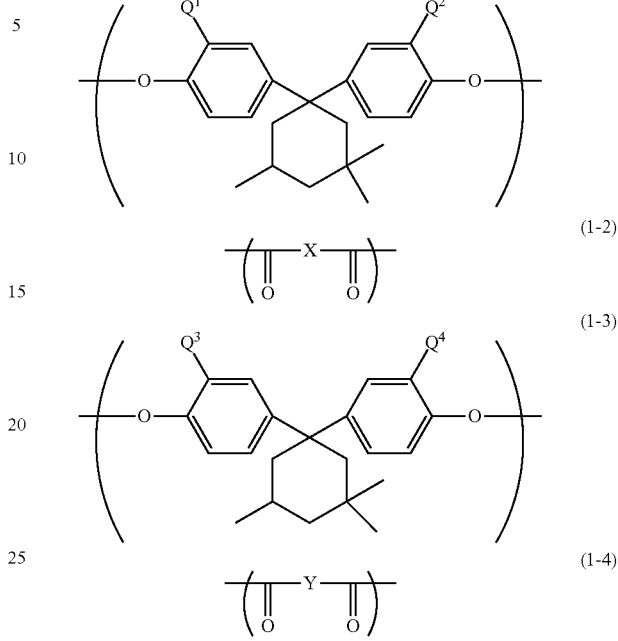

$Q^1$ and $Q^2$ in general formula (1-1), X in general formula (1-2), $Q^3$ and $Q^4$ in general formula (1-3), and Y in general formula (1-4) are respectively the same as defined for $Q^1$, $Q^2$, X, $Q^3$, $Q^4$, and Y in general formula (1).

Note that r in general formula (1) represents a percentage of the number of the repeating units (1-1) relative to a sum of the number of the repeating units (1-1), the number of the repeating units (1-2), the number of the repeating units (1-3), and the number of the repeating units (1-4) in the polyarylate resin (1). s represents a percentage of the number of the repeating units (1-2) relative to the sum of the number of the repeating units (1-1), the number of the repeating units (1-2), the number of the repeating units (1-3), and the number of the repeating units (1-4) in the polyarylate resin (1). t represents a percentage of the number of the repeating units (1-3) relative to the sum of the number of the repeating units (1-1), the number of the repeating units (1-2), the number of the repeating units (1-3), and the number of the repeating units (1-4) in the polyarylate resin (1). u represents a percentage of the number of the repeating units (1-4) relative to the sum of the number of the repeating units (1-1), the number of the repeating units (1-2), the number of the repeating units (1-3), and the number of the repeating units (1-4) in the polyarylate resin (1). Note that each of r, s, t, and u is not a value obtained from one resin chain but a number average obtained from all molecules of the polyarylate resin (1) (a plurality of resin chains) contained in the photosensitive layer 3.

The polyarylate resin (1) may have another repeating unit in addition to the repeating units (1-1) to (1-4). A ratio (mole fraction) of a sum of the amounts by mole of the repeating units (1-1) to (1-4) relative to the total amount by mole of all the repeating units included in the polyarylate resin (1) is preferably at least 0.80, more preferably at least 0.90, and still more preferably 1.00.

No particular limitations are placed on the sequence of the repeating units (1-1) to (1-4) in the polyarylate resin (1) so long as a repeating unit derived from an aromatic diol and a repeating unit derived from an aromatic dicarboxylic acid are adjacent to one another. For example, the repeating unit (1-1) is adjacent to and bonded to the repeating unit (1-2) or the repeating unit (1-4). For another example, the repeating unit (1-3) is adjacent to and bonded to the repeating unit (1-2) or the repeating unit (1-4).

Examples of the polyarylate resin (1) include polyarylate resins represented by chemical formulae (R-1) to (R-1) shown below (also referred to below as polyarylate resins (R-1) to (R-11), respectively).

[Formula 27]

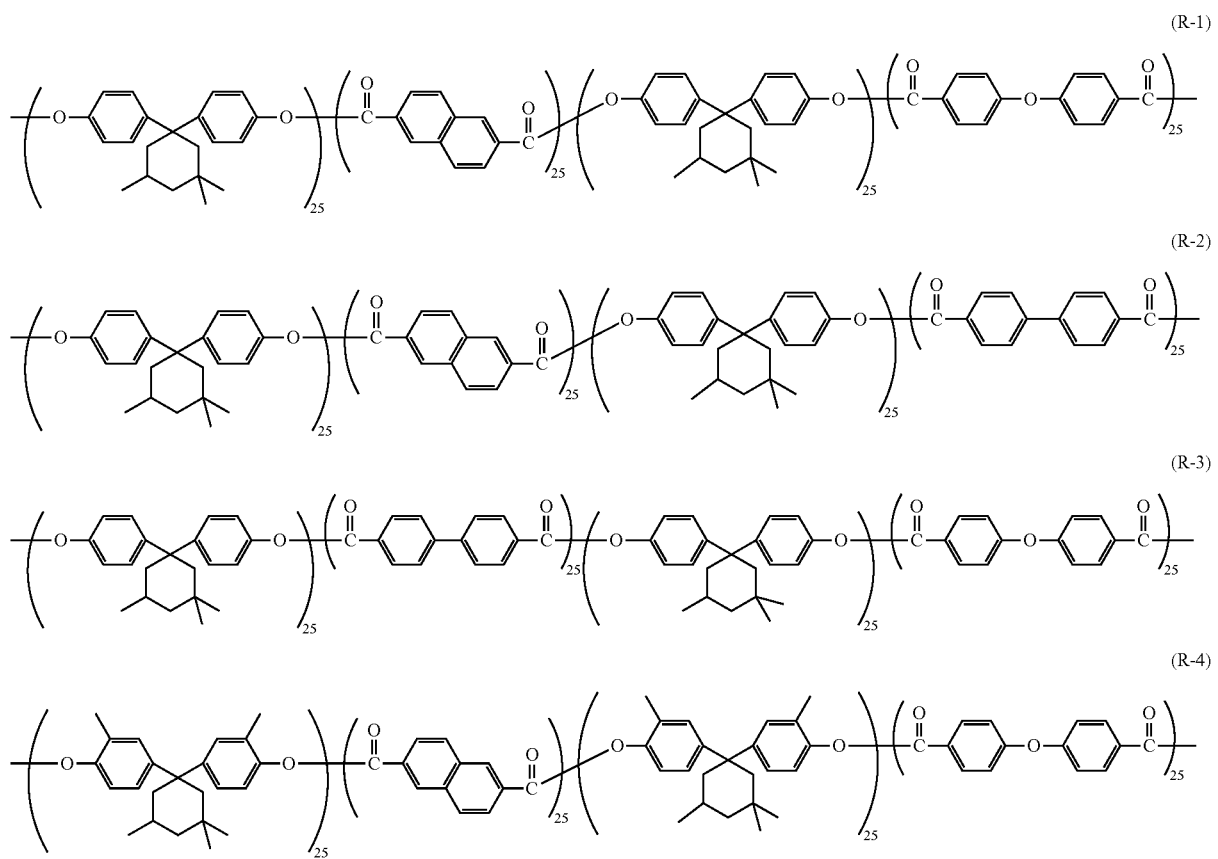

[Formula 28]

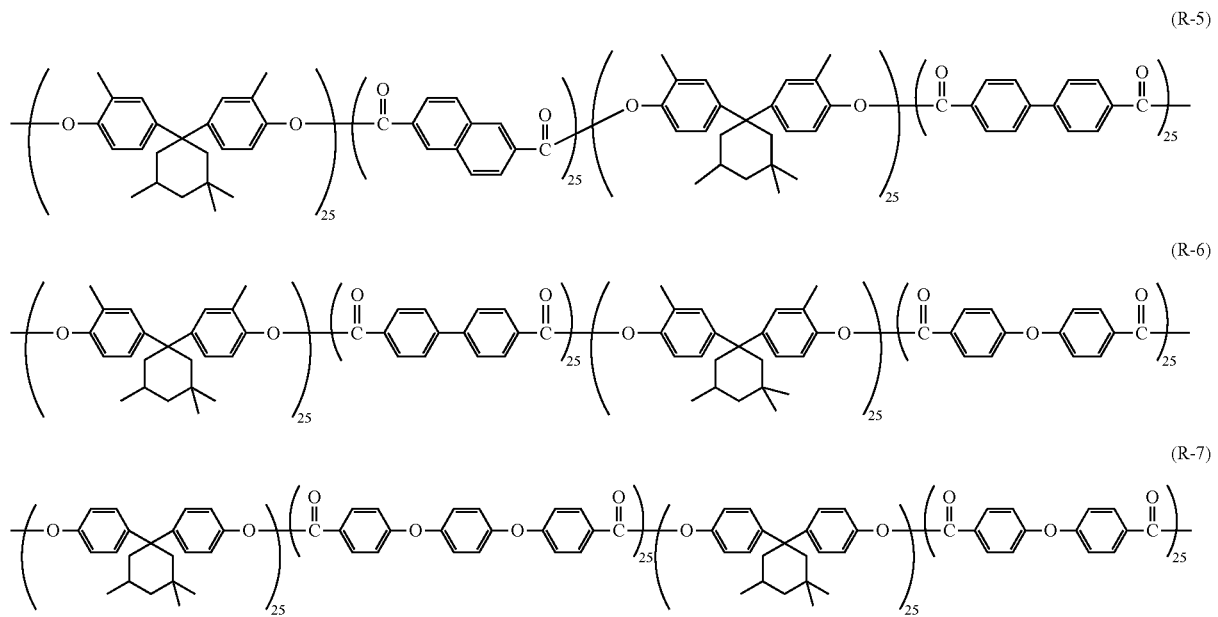

[Formula 29]

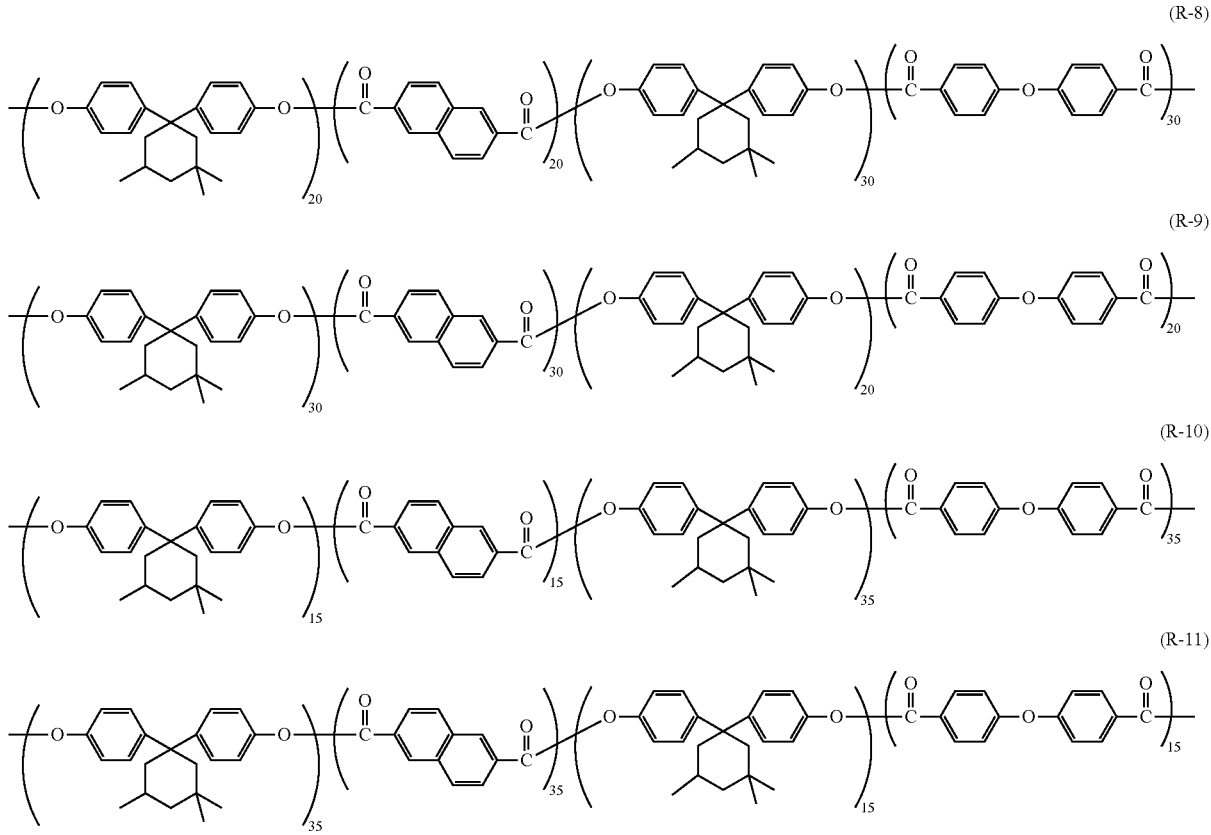

The binder resin preferably has a viscosity average molecular weight of at least 20,000, more preferably at least 25,000, and still more preferably at least 30,000. The viscosity average molecular weight of the binder resin is preferably no greater than 70,000, more preferably no greater than 50,000, and still more preferably no greater than 40,000. As a result of the viscosity average molecular weight of the binder resin being at least 30,000, the binder resin can have improved abrasion resistance, preventing the photosensitive layer 3 from being easily abraded. As a result of the viscosity average molecular weight of the binder resin being no greater than 40,000, the binder resin dissolves more readily in a solvent in formation of the photosensitive layer 3, and thus the photosensitive layer 3 tends to be readily formed.

As the binder resin, the polyarylate resin (1) may be used independently, or a resin (an additional resin) other than the polyarylate resin (1) may be used. Examples of additional resins include thermoplastic resins (specific examples include polyarylate resins other than the polyarylate resin (1), polycarbonate resins, styrene-based resins, styrene-butadiene copolymers, styrene-acrylonitrile copolymers, styrene-maleate copolymers, styrene-acrylate copolymers, acrylic copolymers, polyethylene resins, ethylene-vinyl acetate copolymers, chlorinated polyethylene resins, polyvinyl chloride resins, polypropylene resins, ionomers, vinyl chloride-vinyl acetate copolymers, polyester resins, alkyd resins, polyamide resins, polyurethane resins, polysulfone resins, diallyl phthalate resins, ketone resins, polyvinyl butyral resins, polyether resins, and polyester resins), thermosetting resins (specific examples include silicone resins, epoxy resins, phenolic resins, urea resins, melamine resins, and other crosslinkable thermosetting resins), and photocurable resins (specific examples include epoxy-acrylate-based resins and urethane-acrylate-based copolymers). Any one of the resins listed above may be used independently, or any two or more of the resins listed above may be used in combination.

(Preparation Method of Binder Resin)

No particular limitations are placed on the method for preparing the binder resin so long as the method enables preparation of the polyarylate resin (1). Examples of preparation methods (synthesis methods) of the polyarylate resin (1) include a method involving polycondensation of an aromatic dicarboxylic acid and an aromatic diol for forming repeating units of the polyarylate resin (1). No particular limitations are placed on the specific synthesis method of the polyarylate resin (1), and a known synthesis method (specific examples include solution polymerization, melt polymerization, and interfacial polymerization) can be employed. The following describes an example of the synthesis method of the polyarylate resin (1).

The polyarylate resin (1) is for example prepared through a method involving a reaction represented by chemical equation (R1) shown below (also referred to below as a reaction (R1)) or through a method conforming therewith. The preparation method of the polyarylate resin for example includes the reaction (R1).

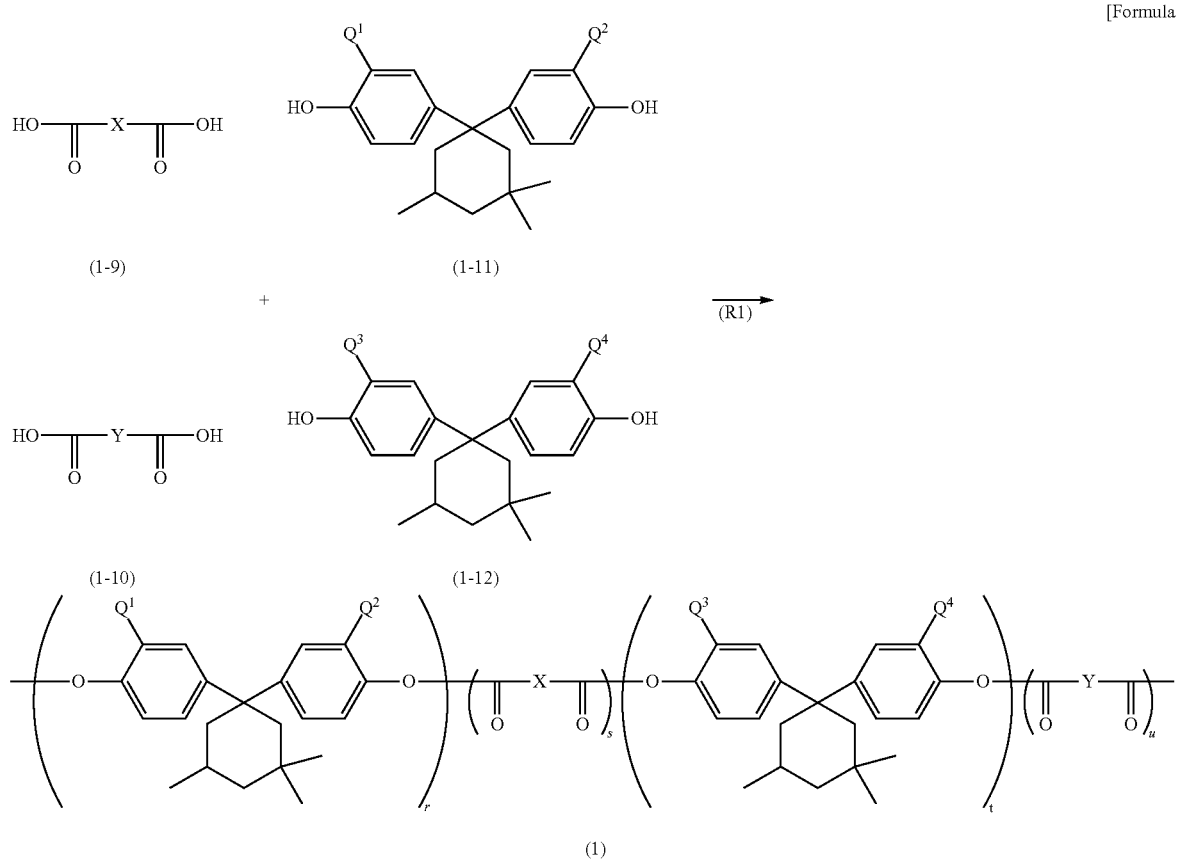

In the reaction (R1), $Q^1$ and $Q^2$ in general formula (1-11), $Q^3$ and $Q^4$ in general formula (1-12), X in general formula (1-9), and Y in general formula (1-10) are respectively the same as defined for $Q^1$, $Q^2$, $Q^3$, $Q^4$, X, and Y in general formula (1).

In the reaction (R1), a reaction is caused between an aromatic dicarboxylic acid represented by general formula (1-9) and an aromatic dicarboxylic acid represented by general formula (1-10) (also referred to below as an aromatic dicarboxylic acid (1-9) and an aromatic dicarboxylic acid (1-10), respectively), and an aromatic diol represented by general formula (1-11) and an aromatic diol represented by general formula (1-12) (also referred to below as an aromatic diol (1-11) and an aromatic diol (1-12), respectively) to obtain the polyarylate resin (1).

Preferably, a sum of an amount by mole of the aromatic diol (1-11) and an amount by mole of the aromatic diol (1-12) is at least 0.9 mol and no greater than 1.1 mol relative to 1 mol of a sum of an amount by mole of the aromatic dicarboxylic acid (1-9) and an amount by mole of the aromatic dicarboxylic acid (1-10). As a result of the aromatic diols and the aromatic dicarboxylic acids being in the above-specified amount range, the polyarylate resin (1) is readily purified, and the polyarylate resin (1) is obtained in good yield.

The reaction (R1) may be promoted in the presence of an alkali and a catalyst. Examples of catalysts include tertiary ammoniums (specific examples include trialkylamines) and quaternary ammonium salts (specific examples include benzyltrimethylammoniumbromide). Examples of alkalis include alkali metal hydroxides (specific examples include sodium hydroxide and potassium hydroxide) and alkaline earth metal hydroxides (specific examples include calcium hydroxide). The reaction (R1) may be promoted in a solvent under an inert gas atmosphere. The solvent is for example water or chloroform. The inert gas is for example argon. Preferably, the reaction time of the reaction (R1) is at least 2 hours and no greater than 5 hours. Preferably, the reaction temperature is at least 5° C. and no greater than 25° C.

Examples of the aromatic dicarboxylic acids (1-9) and (1-10) include aromatic dicarboxylic acids having two carboxyl groups each bonded to an aromatic ring (specific examples include 2,6-naphthalene dicarboxylic acid, 4,4'-dicarboxydiphenyl ether, and 4,4'-dicarboxybiphenyl). An additional dicarboxylic acid other than the aromatic dicarboxylic acids (1-9) and (1-10) may be used in the reaction (R1). Note that a derivative of an aromatic dicarboxylic acid (specific examples include aryloyl halide and aromatic dicarboxylic acid anhydride) may be used instead of the aromatic dicarboxylic acid (1-9) or (1-10) in the synthesis of the polyarylate resin (1).

Examples of the aromatic diols (1-11) and (1-12) include 1,1-bis(4-hydroxyphenyl)-3,3,5-trimethylcyclohexane and 1,1-bis(4-hydroxy-3-methylphenyl)-3,3,5-trimethylcyclohexane. An additional diol (specific examples include bisphenol A, bisphenol S, bisphenol E, and bisphenol F) other than the aromatic diols (1-11) and (1-12) may be used in the reaction (R1). Note that a derivative such as a diacetate may be used instead of the aromatic diol (1-11) or (1-12) in the synthesis of the polyarylate resin (1).

The preparation of the polyarylate resin (1) may include an optional process (for example, a purification process) as necessary. In the purification process, purification is for example performed by a known method (specific examples include filtration, chromatography, and crystallization).

(Additive)

An additive may be added as an optional component. Examples of additives include antidegradants (specific examples include antioxidants, radical scavengers, quenchers, and ultraviolet absorbing agents), softeners, surface modifiers, extenders, thickeners, dispersion stabilizers, waxes, donors, surfactants, and leveling agents. Any one of the additives listed above may be added independently, or any two or more of the additives listed above may be added in combination.

Examples of antioxidants include hindered phenol compounds, hindered amine compounds, thioether compounds, and phosphite compounds. Of the antioxidants listed above, hindered phenol compounds and hindered amine compounds are preferable.

[3. Intermediate Layer]

As described above, the photosensitive member 1 according to the present embodiment may have the intermediate layer 4 (for example, an undercoat layer). The intermediate layer 4 for example contains inorganic particles and a resin that is used for the intermediate layer (an intermediate layer resin). Provision of the intermediate layer 4 can facilitate flow of current generated when the photosensitive member 1 is exposed to light and inhibit increasing resistance, while also maintaining insulation to a sufficient degree so as to inhibit occurrence of leakage current.

Examples of inorganic particles include particles of metals (specific examples include aluminum, iron, and copper), particles of metal oxides (specific examples include titanium oxide, alumina, zirconium oxide, tin oxide, and zinc oxide), and particles of non-metal oxides (specific examples include silica). Any one type of the inorganic particles listed above may be used independently, or any two or more types of the inorganic particles listed above may be used in combination. The inorganic particles may be surface-treated.

No particular limitations are placed on the intermediate layer resin other than being a resin that can be used for forming the intermediate layer.

[4. Photosensitive Member Production Method]

The following describes a production method of the photosensitive member 1. The production method of the photosensitive member 1 for example includes a photosensitive layer formation process. In the photosensitive layer formation process, an application liquid for formation of the photosensitive layer 3 (also referred to below as an application liquid for photosensitive layer formation) is prepared. Next, the application liquid for photosensitive layer formation is applied onto the conductive substrate 2. Next, drying is performed by an appropriate method to remove at least a portion of a solvent in the applied application liquid for photosensitive layer formation. Thus, the photosensitive layer 3 is formed. The application liquid for photosensitive layer formation for example contains a charge generating material, a hole transport material, an electron transport material, the polyarylate resin (1) as a binder resin, and a solvent. The application liquid for photosensitive layer formation is prepared by dissolving or dispersing the charge generating material, the hole transport material, the electron transport material, and the polyarylate resin (1) as the binder resin in the solvent. Additives may optionally be added to the application liquid for photosensitive layer formation.

The following describes the photosensitive layer formation process in detail. No particular laminations are placed on the solvent contained in the application liquid for photosensitive layer formation other than that components of the application liquid should be soluble or dispersible in the solvent. Examples of solvents include alcohols (specific examples include methanol, ethanol, isopropanol, and butanol), aliphatic hydrocarbons (specific examples include n-hexane, octane, and cyclohexane), aromatic hydrocarbons (specific examples include benzene, toluene, and xylene), halogenated hydrocarbons (specific examples include dichloromethane, dichloroethane, carbon tetrachloride, and chlorobenzene), ethers (specific examples include dimethyl ether, diethyl ether, tetrahydrofuran, ethylene glycol dimethyl ether, and diethylene glycol dimethyl ether), ketones (specific examples include acetone, methyl ethyl ketone, and cyclohexanone), esters (specific examples include ethyl acetate and methyl acetate), dimethyl formaldehyde, dimethyl formamide, and dimethyl sulfoxide. Any one of the solvents listed above may be used independently, or any two or more of the solvents listed above may be used in combination. Of the solvents listed above, a non-halogenated solvent is preferably used.

The application liquid for photosensitive layer formation is prepared by mixing the components to disperse the components in the solvent. Mixing or dispersion can for example be performed using a bead mill, a roll mill, a ball mill, an attritor, a paint shaker, or an ultrasonic disperser.

The application liquid for photosensitive layer formation may for example contain a surfactant or a leveling agent in order to improve dispersibility of the components or improve surface flatness of the resulting photosensitive layer 3.

No particular limitations are placed on the method by which the application liquid for photosensitive layer formation is applied so long as the method enables uniform application of the application liquid for photosensitive layer formation. Examples of application methods include dip coating, spray coating, spin coating, and bar coating.

No particular limitations are placed on the method by which at least a portion of the solvent in the application liquid for photosensitive layer formation is removed other than being a method that enables evaporation of at least a portion of the solvent in the application liquid. Examples of methods that can be used to remove the solvent include heating, pressure reduction, and a combination of heating and pressure reduction. One specific example of the method involves heat treatment (hot-air drying) using a high-temperature dryer or a reduced pressure dryer. The heat treatment is for example performed for at least 3 minutes and no greater than 120 minutes at a temperature of at least 40° C. and no greater than 150° C.

Note that the production method of the photosensitive member 1 may further include an optional process such as a process of forming the intermediate layer 4 as necessary. The process of forming the intermediate layer 4 can be carried out by a method selected appropriately from known methods.

The photosensitive member according to the present embodiment described above is excellent in anti-fogging performance, and can therefore be favorably used in various image forming apparatuses.

Second Embodiment: Image Forming Apparatus

The following describes an image forming apparatus according to a second embodiment. The image forming apparatus according to the second embodiment includes an image bearing member, a charger, a light exposure section, a development section, and a transfer section. The image bearing member is the photosensitive member according to the first embodiment described above. The charger charges a surface of the image bearing member. The charger has a positive charging polarity. The light exposure section exposes the charged surface of the image bearing member to light to form an electrostatic latent image on the surface of the image bearing member. The development section develops the electrostatic latent image into a toner image. The transfer section transfers the toner image from the image bearing member to a transfer target while bringing the transfer target into contact with the surface of the image bearing member.

The image forming apparatus according to the second embodiment can inhibit image defects from occurring. The reason for the above is thought to be as follows. The image forming apparatus according to the second embodiment includes the photosensitive member according to the first embodiment as an image bearing member. The photosensitive member according to the first embodiment is excellent in anti-fogging performance. The image forming apparatus according to the second embodiment can therefore inhibit image defects (specific examples include fogging) from occurring.

Figure 4:
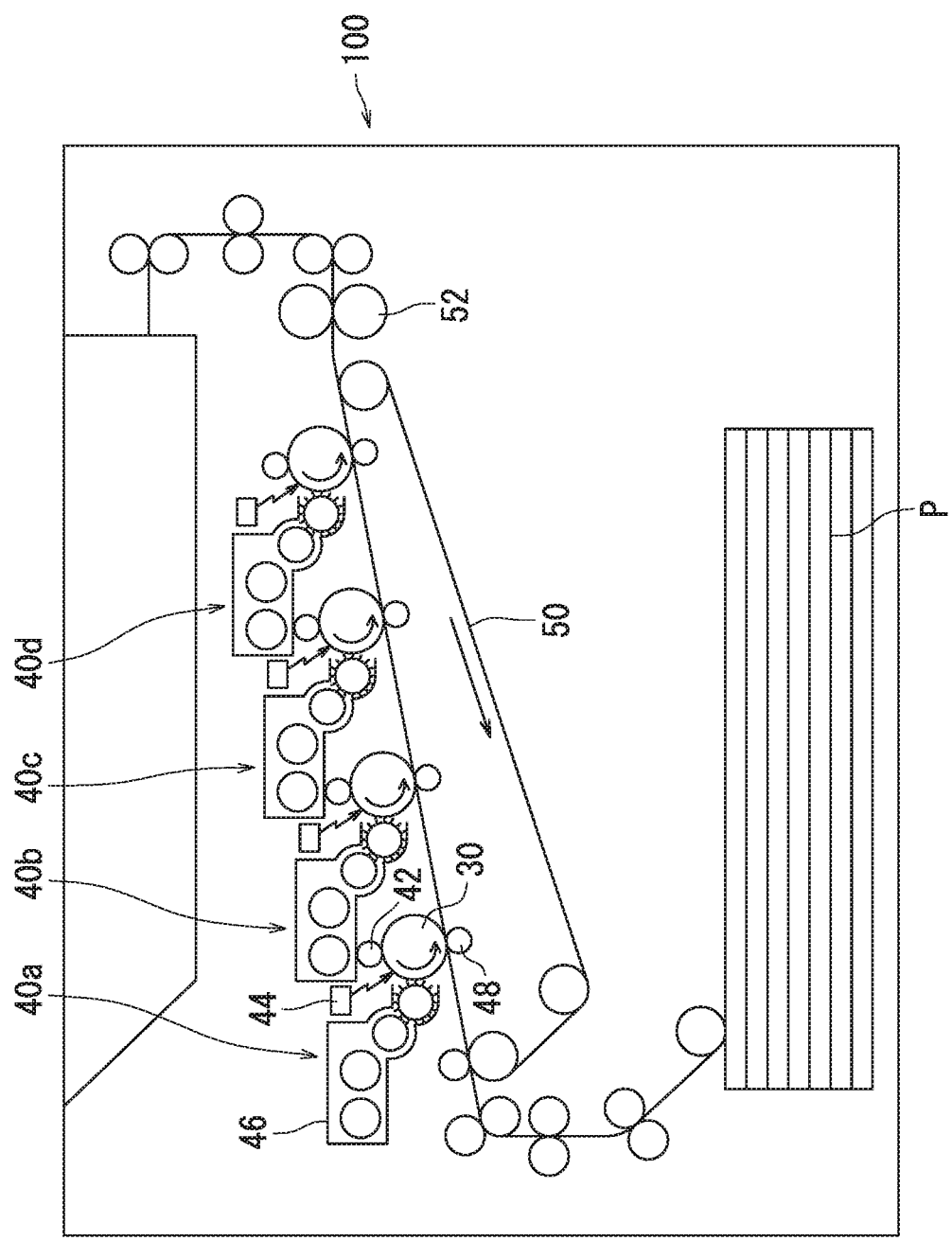
FIG. 4 is a diagram illustrating an example of an image forming apparatus according to a second embodiment of the present invention.

The following describes a tandem color image forming apparatus as an example of the image forming apparatus according to the second embodiment with reference to FIG. 4.

An image forming apparatus 100 illustrated in FIG. 4 adopts a direct transfer process. Typically, a recording medium serving as a transfer target comes in contact with an image bearing member in an image forming apparatus adopting the direct transfer process. As a result, minute matter from the recording medium is likely to adhere to a surface of the image bearing member and cause an image defect. However, the image forming apparatus 100, which is an example of the second embodiment, includes the photosensitive member according to the first embodiment as an image bearing member 30. The photosensitive member according to the first embodiment is excellent in anti-fogging performance. Accordingly, as long as the image forming apparatus 100 includes the photosensitive member according to the first embodiment as the image bearing member 30, it is possible to inhibit image defects from occurring even if the image forming apparatus 100 adopts the direct transfer process.

The image forming apparatus 100 includes image formation units 40a, 40b, 40c, and 40d, a transfer belt 50, and a fixing section 52. Hereinafter, the image formation units 40a, 40b, 40c, and 40d are each referred to as an image formation unit 40 unless they need to be distinguished from one another.

The image formation unit 40 includes the image bearing member 30, a charger 42, a light exposure section 44, a development section 46, and a transfer section 48. The image bearing member 30 is located at a central location in the image formation unit 40. The image bearing member 30 is rotatable in an arrow direction (counterclockwise). The charger 42, the light exposure section 44, the development section 46, and the transfer section 48 are located around the image bearing member 30 in order from upstream in a rotation direction of the image bearing member 30 relative to the charger 42 as a reference point. Note that the image formation unit 40 may further include a cleaning section (not shown) or a static eliminating section (not shown).

The image formation units 40a to 40d respectively superimpose toner images of a plurality of colors (for example, four colors including black, cyan, magenta, and yellow) in order on a recording medium P on the transfer belt 50.

The charger 42 is a charging roller. The charging roller charges a surface of the image bearing member 30 while in contact with the surface of the image bearing member 30. Typically, image defects easily occur in the case of an image forming apparatus including a charging roller. However, the image forming apparatus 100 includes the photosensitive member according to the first embodiment as the image bearing member 30. The photosensitive member according to the first embodiment is excellent in anti-fogging performance. It is therefore possible to inhibit image defects from occurring even if the image forming apparatus 100 includes a charging roller as the charger 42. As described above, the image forming apparatus 100, which is an example of the second embodiment, adopts a contact charging process. Another example of the contact charger is a charging brush. Note that the charger may be a non-contact charger. Examples of the non-contact charger include a corotron charger and a scorotron charger.

No particular limitations are placed on the voltage that is applied by the charger 42. The voltage that is applied by the charger 42 is for example a direct current voltage, an alternating current voltage, or a composite voltage (of an alternating current voltage superimposed on a direct current voltage), among which a direct current voltage is preferable. The direct current voltage is advantageous as described below compared to an alternating current voltage and a composite voltage. In a configuration in which the charger 42 only applies a direct current voltage, the value of voltage applied to the image bearing member 30 is constant, and therefore it is easy to uniformly charge the surface of the image bearing member 30 to a specified potential. The amount of abrasion of the photosensitive layer tends to be smaller in a configuration in which the charger 42 only applies a direct current voltage. As a result, favorable images can be formed.

The light exposure section 44 exposes the charged surface of the image bearing member 30 to light. As a result, an electrostatic latent image is formed on the surface of the image bearing member 30. The electrostatic latent image is formed based on image data input into the image forming apparatus 100.

The development section 46 supplies toner to the surface of the image bearing member 30 to develop the electrostatic latent image into a toner image. The development section 46 may develop the electrostatic latent image into a toner image while in contact with the surface of the image bearing member 30.

The development section 46 is capable of cleaning the surface of the image bearing member 30. That is, the image forming apparatus 100 may adopt a cleaner-less process, which is a process without a cleaner. According to this configuration, the development section 46 is capable of removing residual matter on the surface of the image bearing member 30. A typical image forming apparatus including a cleaning section (for example, a cleaning blade) and an image bearing member scrapes away residual matter on a surface of the image bearing member using the cleaning section. However, the image forming apparatus adopting the cleaner-less process does not scrape away residual matter on the surface of the image bearing member. The image forming apparatus adopting the cleaner-less process therefore tends to leave the residual matter on the surface of the image bearing member. However, the image forming apparatus 100 includes the photosensitive member according to the first embodiment, which is excellent in anti-fogging performance, as the image bearing member 30. As long as the image forming apparatus 100 includes such a photosensitive member, residual matter, particularly minute matter (for example, paper dust) from the recording medium P, tends not to be left on the surface of the photosensitive member even if the image forming apparatus 100 adopts the cleanerless process. As a result, the image forming apparatus 100 is capable of inhibiting image defects (for example, fogging) from occurring.

In order that the development section 46 efficiently cleans the surface of the image bearing member 30 as well as performing development, the following conditions (a) and (b) are preferably satisfied.

Condition (a): A contact development process is adopted, and a peripheral speed (rotation speed) of the image bearing member 30 and a peripheral speed (rotation speed) of the development section 46 are different.

Condition (b): A surface potential of the image bearing member 30 and a potential of development bias satisfy relation (b-1) and relation (b-2) shown below.

0 (V) < Potential (V) of development bias < Surface potential (V)     (b-1)
of non-exposed region of image bearing member 30
Potential (V) of development bias > Surface potential (V) of     (b-2)
exposed region of image bearing member 30 > 0 (V)

When the condition (a) is satisfied, that is, in a configuration in which the contact development process is adopted, and the peripheral speed of the image bearing member 30 and the peripheral speed of the development section 46 are different, the surface of the image bearing member 30 is in contact with the development section 46, and matter adhering to the surface of the image bearing member 30 is removed by rubbing against the development section 46. Preferably, the peripheral speed of the development section 46 is greater than the peripheral speed of the image bearing member 30.

The condition (b) is on the assumption that a reversal development process is adopted. Preferably, in order to improve electrical characteristics of the image bearing member 30 that has a positive charging polarity, all of the charging polarity of the toner, the surface potential of the non-exposed region of the image bearing member 30, the surface potential of the exposed region of the image bearing member 30, and the potential of the development bias are of positive polarity. Note that the surface potential of the non-exposed region of the image bearing member 30 and the surface potential of the exposed region of the image bearing member 30 are measured after toner image transfer from the image bearing member 30 to the recording medium P by the transfer section 48 and before charging of the surface of the image bearing member 30 by the charger 42.

When the relation (b-1) of the condition (b) is satisfied, an electrostatic repulsion between remaining toner (also referred to below as residual toner) on the image bearing member 30 and the non-exposed region of the image bearing member 30 is greater than an electrostatic repulsion between the residual toner and the development section 46. As a result, the residual toner in the non-exposed region of the image bearing member 30 moves from the surface of the image bearing member 30 to the development section 46 to be collected.

When relation (b-2) of the condition (b) is satisfied, an electrostatic repulsion between the residual toner and the exposed region of the image bearing member 30 is smaller than an electrostatic repulsion between the residual toner and the development section 46. As a result, the residual toner in the exposed region of the image bearing member 30 is kept on the surface of the image bearing member 30. The toner kept in the exposed region of the image bearing member 30 is then used for image formation.

The transfer belt 50 conveys the recording medium P to a location between the image bearing member 30 and the transfer section 48. The transfer belt 50 is an endless belt. The transfer belt 50 is rotatable in an arrow direction (clockwise).

After the toner image has been formed through development by the development section 46, the transfer section 48 transfers the toner image from the surface of the image bearing member 30 to the recording medium P. The toner image is transferred from the image bearing member 30 to the recording medium P while the image bearing member 30 is in contact with the recording medium P. The transfer section 48 is for example a transfer roller.

The fixing section 52 applies either or both of heat and pressure to the unfixed toner image transferred to the recording medium P by the transfer section 48. The fixing section 52 is for example either or both of a heating roller and a pressure roller. The toner image is fixed to the recording medium P through application of either or both of heat and pressure to the toner image. As a result, an image is formed on the recording medium P.

An example of the image forming apparatus according to the second embodiment has been described above. However, the image forming apparatus according to the second embodiment is not limited to the image forming apparatus 100 described above. For example, the image forming apparatus according to the second embodiment may be a monochrome image forming apparatus. In this case, for example, it is only necessary that the image forming apparatus includes at least one image formation unit. For another example, the image forming apparatus according to the second embodiment is not limited to the above-described tandem image forming apparatus 100 and may alternatively be a rotary image forming apparatus. The image forming apparatus according to the second embodiment may adopt an intermediate transfer process. In a configuration in which the image forming apparatus according to the second embodiment adopts an intermediate transfer process, the transfer target is an intermediate transfer belt.

Third Embodiment: Process Cartridge

A process cartridge according to a third embodiment includes the photosensitive member according to the first embodiment as an image bearing member. The following describes an example of the process cartridge according to the third embodiment with reference to FIG. 4.

The process cartridge according to the third embodiment is for example equivalent to each of the image formation units 40a to 40d (FIG. 4). Each of the process cartridges has a unitized configuration. The unitized configuration includes the image bearing member 30. The unitized configuration may include, in addition to the image bearing member 30, at least one selected from the group consisting of the charger 42, the light exposure section 44, the development section 46, and the transfer section 48. The process cartridge may further include a static eliminating section (not shown). The process cartridge is for example designed to be freely attachable to and detachable from the image forming apparatus 100. Accordingly, the process cartridge is easy to handle and can be easily and quickly replaced, together with the image bearing member 30, when properties such as sensitivity of the image bearing member 30 deteriorate.

The process cartridge according to the third embodiment described above includes the photosensitive member according to the first embodiment as an image bearing member, and thus is capable of inhibiting image defects from occurring.

EXAMPLES

The following provides more specific description of the present invention through use of Examples. Note that the present invention is not limited to the scope of the Examples.
<Materials Used in Examples and Comparative Examples>

A charge generating material, a hole transport material, electron transport materials, and binder resins described below were prepared as materials for production of single-layer photosensitive members.
[Charge Generating Material]

The charge generating material (CGM-1) described in association with the first embodiment was prepared. The charge generating material (CGM-1) was metal-free phthalocyanine represented by chemical formula (CGM-1) having an X-form crystal structure. That is, the charge generating material (CGM-1) was X-form metal-free phthalocyanine.
[Hole Transport Material]

The hole transport material (HTM1-1) described in association with the first embodiment was prepared.
[Electron Transport Material]

The electron transport materials (ETM1-1), (ETM2-1), (ETM3-1), (ETM4-1), and (ETM5-1) described in association with the first embodiment were prepared. Furthermore, electron transport materials (ETM6-1) and (ETM7-1) were also prepared. The electron transport materials (ETM6-1) and (ETM7-1) are respectively electron transport materials represented by chemical formulae (ETM6-1) and (ETM7-1) shown below.

[Formula 31]

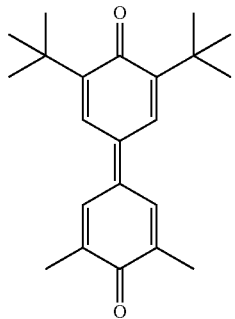

(ETM6-1)

[Formula 32]

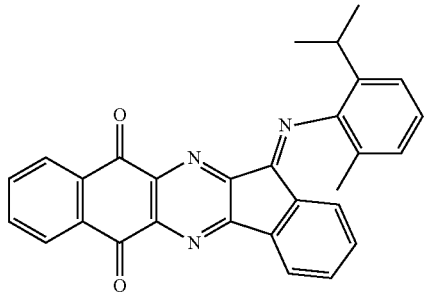

(ETM7-1)

[Binder Resin]

The polyarylate resins (R-1) to (R-9) described in association with the first embodiment and polyarylate resins (R-12) to (R-17) were prepared as the binder resins. The resins (R-12) to (R-17) are resins including repeating units represented by chemical formulae (R-12) to (R-17) shown below, respectively.

[Formula 33]

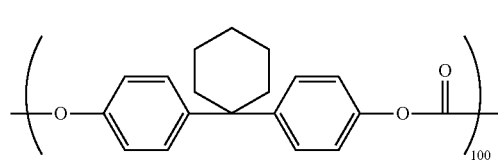

(R-12)

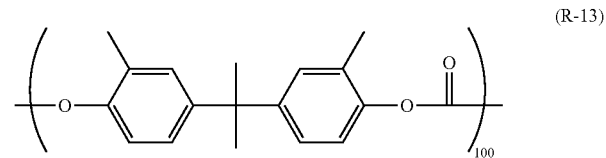

(R-13)

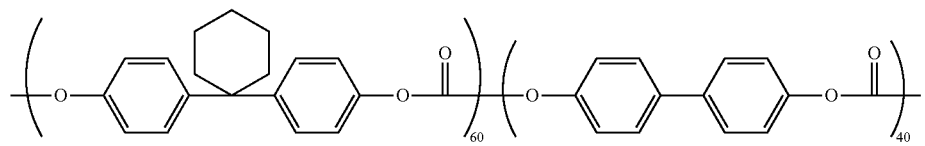

(R-14)

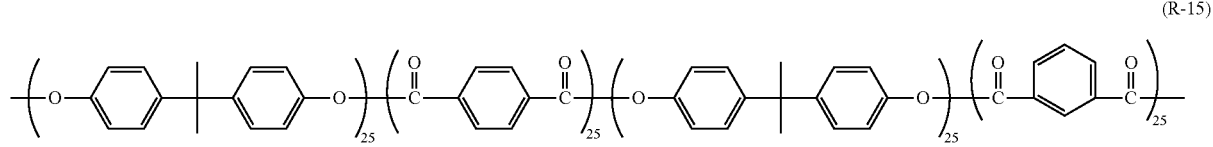

(R-15)

[Formula 34]

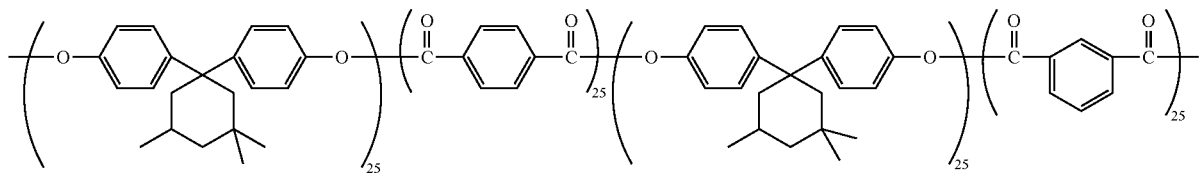

(R-16)

[Formula 35]

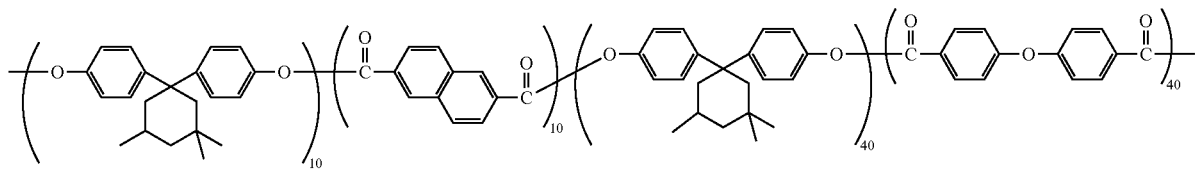

-continued

The following describes synthesis methods of the polyarylate resins (R-1) to (R-9) that were used in the Examples.

(Synthesis Method of Polyarylate Resin (R-1))

A three-necked flask was used as a reaction vessel. The reaction vessel was a three-necked flask having a capacity of 1 L and equipped with a thermometer, a three-way cock, and a dripping funnel. Into the reaction vessel, 25.63 g (82.86 mmol) of 1,1-bis(4-hydroxyphenyl)-3,3,5-trimethylcyclohexane, 0.124 g (0.826 mmol) of t-butylphenol, 7.84 g (196 mmol) of sodium hydroxide, and 0.240 g (0.768 mmol) of benzyltributylammonium chloride were added. Next, the reaction vessel was purged with argon. Thereafter, 600 mL of water was added into the reaction vessel. The internal temperature of the reaction vessel was kept at 20° C., and the reaction vessel contents were stirred for 1 hour. Thereafter, the internal temperature of the reaction vessel was reduced to 10° C. As a result, an alkaline aqueous solution was obtained.

Separately from the alkaline aqueous solution, 9.84 g (38.9 mmol) of 2,6-naphthalenedicarboxylic acid dichloride and 11.47 g (38.9 mmol) of 4,4'-oxybisbenzoic acid dichloride were dissolved in 300 g of chloroform. As a result, a chloroform solution was obtained.

Next, the temperature of the alkaline aqueous solution was adjusted to 10° C., and subsequently the chloroform solution was gradually dripped into the alkaline aqueous solution through the dripping funnel over 110 minutes to initiate a polymerization reaction. The polymerization reaction was caused to proceed for 3 hours while the reaction vessel contents were stirred and the internal temperature of the reaction vessel was kept at 13±3° C.

Thereafter, decantation was performed to remove an upper layer (a water layer) from the reaction vessel contents to collect an organic layer. Next, 500 mL of ion exchanged water was added into a three-necked flask having a capacity of 2 L, and then the collected organic layer was added into the flask. Furthermore, 300 g of chloroform and 6 mL of acetic acid were added into the flask. The three-necked flask contents were stirred at room temperature (25° C.) for 30 minutes. Thereafter, decantation was performed to remove an upper layer (a water layer) from the three-necked flask contents to collect an organic layer. The collected organic layer was washed with 500 mL of ion exchanged water using a separatory funnel. Washing with ion exchanged water was repeated eight times, and thus the water-washed organic layer was obtained.

Next, the water-washed organic layer was filtered to collect a filtrate. Into a conical flask having a capacity of 3 L, 1.5 L of methanol was added. The collected filtrate was gradually dripped into the conical flask to give a precipitate. The precipitate was filtered off. The thus collected precipitate was vacuum dried for 12 hours at 70° C. As a result, the polyarylate resin (R-1) was obtained. The mass yield of the polyalylate resin (R-1) was 35.3 g, and the percentage yield thereof was 88.7%.

(Synthesis Method of Polyarylate Resins (R-2) to (R-9))

Each of the polyarylate resins (R-2) to (R-7) was synthesized according to the same method as for the polyarylate resin (R-1) in all aspects other than that 1,1-bis(4-hydroxyphenyl)-3,3,5-trimethylcyclohexane was changed to an aromatic diol that was a starting material of the polyarylate resin, and/or at least one of 2,6-naphthalenedicarboxylic acid dichloride and 4,4'-oxybisbenzoic acid dichloride was changed to an aryloyl halide that was a starting material of the polyarylate resin. Each of the polyarylate resins (R-8) and (R-9) was synthesized according to the same method as for the polyarylate resin (R-1) in all aspects other than that the ratio of the amount by mole of each starting material was changed to the ratio of the amount by mole of the corresponding repeating unit.

Next, a proton nuclear magnetic resonance spectrometer (product of JASCO Corporation, 300 MHz) was used to measure $^1$H-NMR spectra of the polyarylate resins (R-1) to (R-9) synthesized as described above. CDCl$_3$ was used as a solvent. Tetramethylsilane (TMS) was used as an internal standard sample. Of these polyarylate resins, the polyarylate resin (R-1) will be described as a representative example.

FIG. 9 shows a $^1$H-NMR spectrum of the polyarylate resin (R-1). In FIG. 9, the horizontal axis represents chemical shift (unit: ppm) and the vertical axis represents signal intensity (unit: arbitrary unit). Chemical shifts of the polyarylate resin (R-1) are shown below.

Polvarylate resin (R-1): δ=8.81 (d, 2H), 8.17-8.26 (m, 6H), 8.09 (d, 2H), 7.02-7.48 (m, 20H), 2.74 (brs, 2H), 2.50 (brs, 2H), 2.02 (brm, 4H), 1.41 (brs, 2H), 1.23 (brs, 2H), 0.99 (d, 12H), 0.42 (d, 6H).

The $^1$H-NMR spectrum and the chemical shifts were used to confirm that the polyarylate resin (R-1) had been obtained. Likewise, the $^1$H-NMR spectra and chemical shifts of the other polyarylate resins (R-2) to (R-9) were used to confirm that the polyarylate resins (R-2) to (R-9) had been obtained.

<Production of Photosensitive Members>
[Photosensitive Member (A-1)]

The following describes a production method of a photosensitive member (A-1) according to Example 1. A vessel was charged with 2 parts by mass of the charge generating material (CGM-1), 65 parts by mass of the hole transport material (HTM1-1), 35 parts by mass of the electron transport material (ETM3-1), 100 parts by mass of the polyarylate resin (R-1) as a binder resin, and 300 parts by mass of tetrahydrofuran as a solvent. A rod-shaped ultrasonic vibrator was used to mix the materials and the solvent in the vessel for 2 minutes to disperse the materials in the solvent. The materials and the solvent in the vessel were further mixed for 50 hours using a ball mill to disperse the materials in the solvent. Thus, an application liquid for single-layer photosensitive layer formation was obtained. The application liquid for single-layer photosensitive layer formation was applied onto a conductive substrate—an aluminum drum-shaped support—by dip coating. The applied application liquid for single-layer photosensitive layer formation was hot-air dried at 100° C. for 40 minutes. Thus, a single-layer photosensitive layer (film thickness: 25 μm) was formed on the conductive substrate. As a result, the single-layer photosensitive member (A-1) was obtained.

[Photosensitive Members (A-2) to (A-19) and (B-1) to (B-10)]

Photosensitive members (A-2) to (A-19) and (B-1) to (B-10) were obtained according to the same method as the above-described production method of the photosensitive member (A-1) in all aspects other than that the binder resins and the electron transport materials shown in Tables 1 and 2 were used. Note that R-1 to R-9 under "Type" in the column titled "Binder resin" in Tables 1 and 2 respectively represent the polyarylate resins (R-1) to (R-9). R-12 to R-17 under "Type" in the column titled "Binder resin" respectively represent the resins (R-12) to (R-17). "Molecular weight" in the column titled "Binder resin" represents the viscosity average molecular weight of the binder resins. ETM1-1 to ETM7-1 under "Type" in the column titled "Electron transport material" respectively represent the electron transport materials (ETM1-1) to (ETM7-1).

<Measurement Method and Evaluation Method>
[Measurement of Scratch Depth]

With respect to each of the photosensitive members (A-1) to (A-19) and (B-1) to (B-10) obtained as described above, the scratch depth of the photosensitive layer (single-layer photosensitive layer) of the photosensitive member was measured. The scratch depth was measured according to a method described below using a scratching apparatus 200 (see FIG. 5) in accordance with Japanese Industrial Standard (JIS) K5600-5-5 (K5600: testing methods for paints, Part 5: mechanical property of film, Section 5: scratch hardness (stylus method)).

Figure 5:
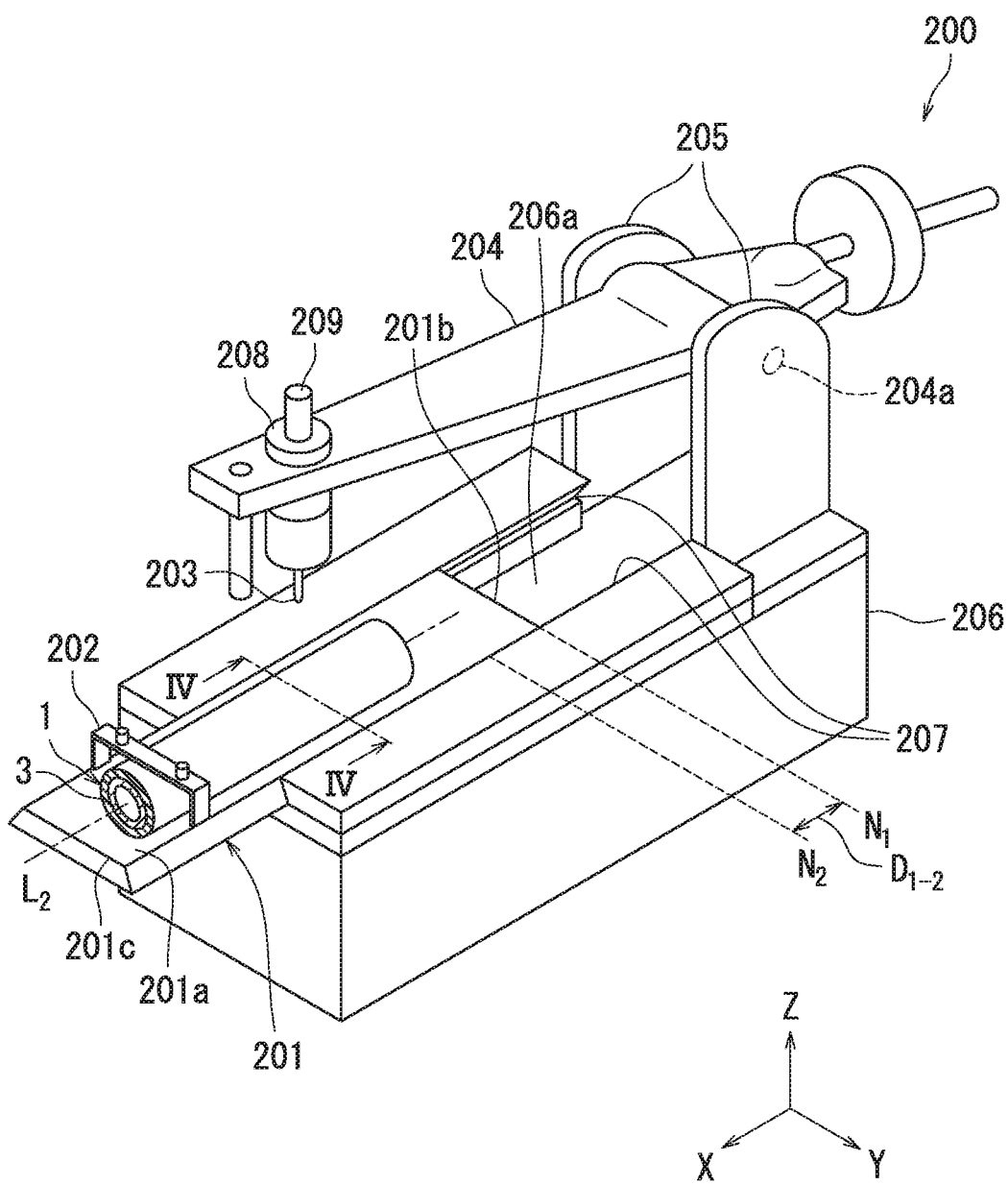
FIG. 5 is a diagram illustrating an example of a configuration of a scratching apparatus.

The following describes the scratching apparatus 200 in accordance with JIS K5600-5-5 with reference to FIG. 5. FIG. 5 is a diagram illustrating an example of a configuration of the scratching apparatus 200. The scratching apparatus 200 includes a fixture 201, a retainer 202, a scratching stylus 203, a support arm 204, two shaft supports 205, a base 206, two rails 207, a weight pan 208, and a constant speed motor (not shown). A weight 209 is placed on the weight pan 208.

In FIG. 5, an X axis direction and a Y axis direction are each a horizontal direction, and a Z axis direction is a vertical direction. The X axis direction indicates a longitudinal direction of the fixture 201. The Y axis direction indicates a direction orthogonal to the X axis direction on a plane parallel with an upper surface (loading surface) 201a of the fixture 201. Note that an X axis direction, a Y axis direction, and a Z axis direction in FIGS. 6 to 8 described below are the same as defined in FIG. 5.

The fixture 201 is equivalent to a test piece fixture according to JIS K5600-5-5. The fixture 201 has the upper surface 201a, an end 201b, and an opposite end 201c. The upper surface 201a of the fixture 201 is a horizontal surface. The end 201b faces toward the two shaft supports 205.

The retainer 202 is disposed on the upper surface 201a of the fixture 201 in a position closer to the opposite end 201c than to the end 201b. The retainer 202 fixes a measurement target (the photosensitive member 1) to the upper surface 201a of the fixture 201.

Figure 6:
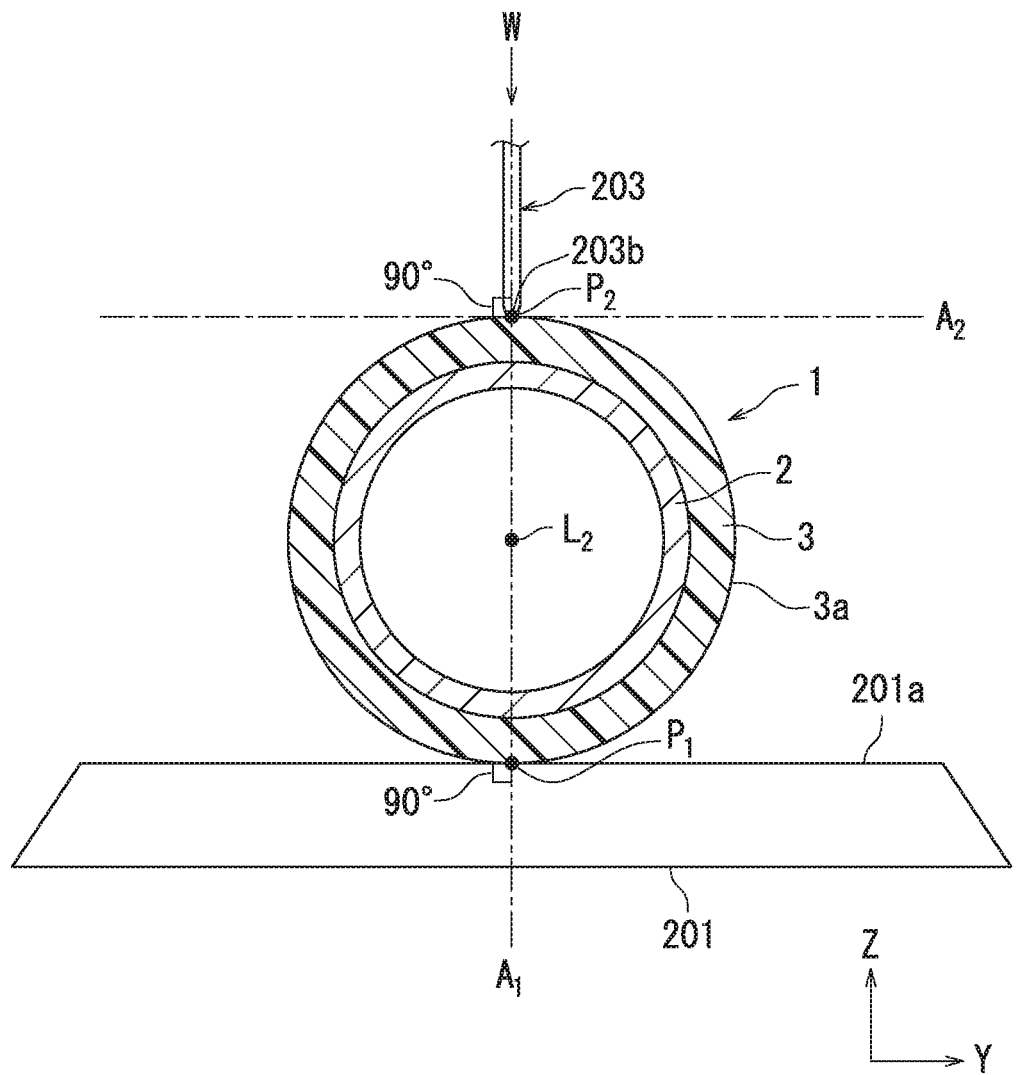
FIG. 6 is a cross-sectional view taken along line IV-IV in FIG. 5.

The scratching stylus 203 has a tip 203b (see FIG. 6). The tip 203b has a semispherical structure having a diameter of 1 mm. The tip 203b is made from sapphire.

The support arm 204 supports the scratching stylus 203. The support arm 204 pivots about a shaft 204a in directions that the scratching stylus 203 moves toward and away from the photosensitive member 1.

The two shaft supports 205 pivotally support the support arm 204.

The base 206 has an upper surface 206a. The two shaft supports 205 are disposed at an end of the upper surface 206a.

The two rails 207 are disposed at an opposite end of the upper surface 206a. The two rails 207 are opposed in parallel with each other. The two rails 207 are parallel with the longitudinal direction (X axis direction) of the fixture 201. The fixture 201 is disposed between the two rails 207. The fixture 201 is horizontally movable along the rails 207 in the longitudinal direction (X axis direction) of the fixture 201.

The weight pan 208 is disposed on the scratching stylus 203 with the support arm 204 therebetween. The weight 209 is placed on the weight pan 208.

The constant speed motor causes the fixture 201 to move along the rails 207 in the longitudinal direction (X axis direction) thereof.

The following describes a measurement method of the scratch depth. The measurement method of the scratch depth includes first to fourth steps. A surface property tester ("HEIDON TYPE 14", product of Shinto Scientific Co., Ltd.) was used as the scratching apparatus 200. The scratch depth was measured under environmental conditions of a temperature of 23° C. and a relative humidity of 50%. The photosensitive member was drum-shaped (cylindrical).

(First Step)

In the first step, the photosensitive member 1 was fixed to the upper surface 201a of the fixture 201 with a longitudinal direction of the photosensitive member 1 parallel with the longitudinal direction of the fixture 201. The photosensitive member 1 was loaded such that a direction of a central axis $L_2$ (rotation axis) of the photosensitive member 1 was parallel with the longitudinal direction of the fixture 201.

(Second Step)

In the second step, the scratching stylus 203 was brought into vertical contact with a surface 3a of a photosensitive layer 3. The following describes how the scratching stylus 203 was brought into vertical contact with the surface 3a of the photosensitive layer 3 of the drum-shaped photosensitive member 1 with reference to FIGS. 6 and 7 in addition to FIG. 5.

Figure 7:
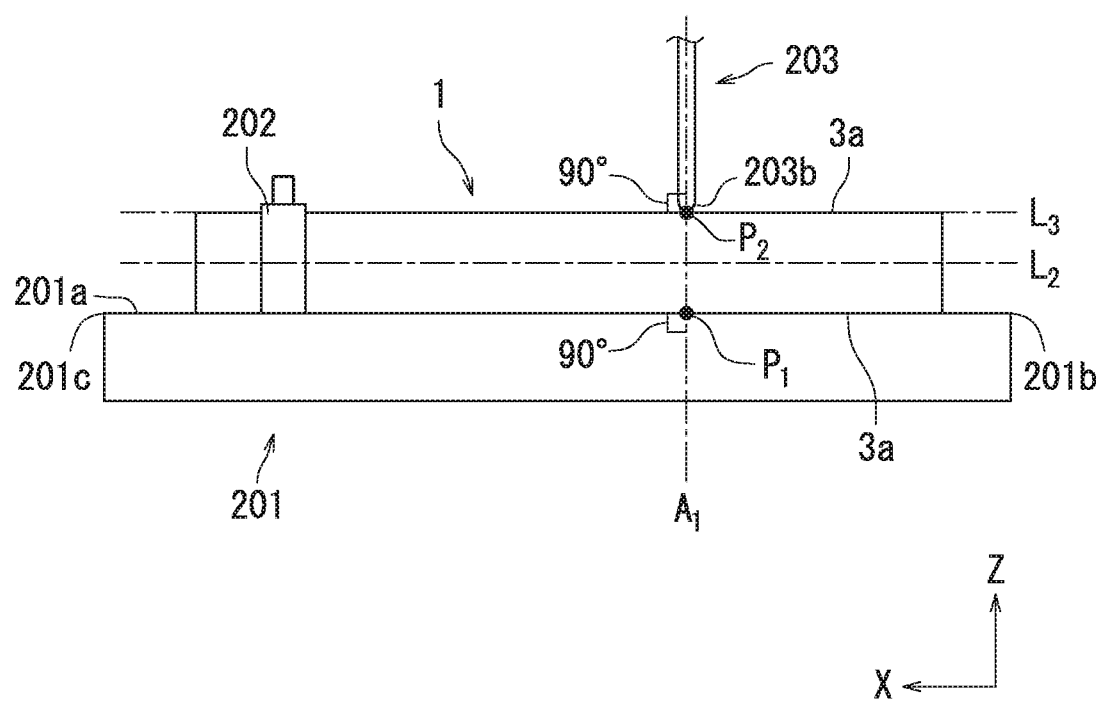
FIG. 7 is a side view of a fixture, a scratching stylus, and an electrophotographic photosensitive member illustrated in FIG. 5.

FIG. 6 is a cross-sectional view of the photosensitive member 1 in contact with the scratching stylus 203, taken along line IV-IV in FIG. 5. FIG. 7 is a side view of the fixture 201, the scratching stylus 203, and the photosensitive member 1 illustrated in FIG. 5.

The scratching stylus 203 was moved toward the photosensitive member 1 such that an extension of a central axis $A_1$ of the scratching stylus 203 was perpendicular to the upper surface 201a of the fixture 201. Next, the tip 203b of the scratching stylus 203 was brought into contact with a point (contact point $P_2$) on the surface 3a of the photosensitive layer 3 of the photosensitive member 1. The location of the contact point $P_2$ was farthest from the upper surface 201a of the fixture 201 in the vertical direction (Z axis direction) among possible locations on the surface 3a. Thus, the tip 203b of the scratching stylus 203 was brought into contact with the photosensitive member 1 such that the central axis $A_1$ of the scratching stylus 203 was perpendicular to a tangent $A_2$. In such an arrangement, a line connecting a contact point $P_1$ in contact with the upper surface 201a and the contact point $P_2$ in contact with the tip 203b was perpendicular to the central axis $L_2$ of the photosensitive member 1. The tangent $A_2$ touches, at the contact point $P_2$, a perimeter circle of a cross-section of the photosensitive member 1 taken in a direction perpendicular to the central axis $L_2$.

(Third Step)

The following describes the third step with reference to FIGS. 5 and 6. In the third step, a load W of 10 g was applied from the scratching stylus 203 to the photosensitive layer 3 with the scratching stylus 203 in vertical contact with the surface 3a of the photosensitive layer 3. Specifically, the weight 209, which weighed 10 g, was placed on the weight pan 208. With the load W being applied to the photosensitive layer 3, the fixture 201 was caused to move. Specifically, the constant speed motor was driven to cause the fixture 201 to horizontally move in the longitudinal direction thereof (X axis direction) along the rails 207. That is, the end 201b of the fixture 201 moved from a first position $N_1$ to a second position $N_2$. The second position $N_2$ was located downstream of the first position $N_1$ in terms of a direction that the fixture 201 moves away from the two shaft supports 205 in the longitudinal direction of the fixture 201. The photosensitive member 1 horizontally moved in the longitudinal direction of the fixture 201 as the fixture 201 moved in the longitudinal direction. The fixture 201 and the photosensitive member 1 moved at a rate of 30 mm/minute. The fixture 201 and the photosensitive member 1 moved by a distance of 30 mm. The distance by which the fixture 201 and the photosensitive member 1 moved was equal to a distance $D_{1-2}$ between the first position $N_1$ and the second position $N_2$. As a result of the fixture 201 and the photosensitive member 1 moving, the scratching stylus 203 created a scratch S on the surface 3a of the photosensitive layer 3 of the photosensitive member 1.

Figure 8:
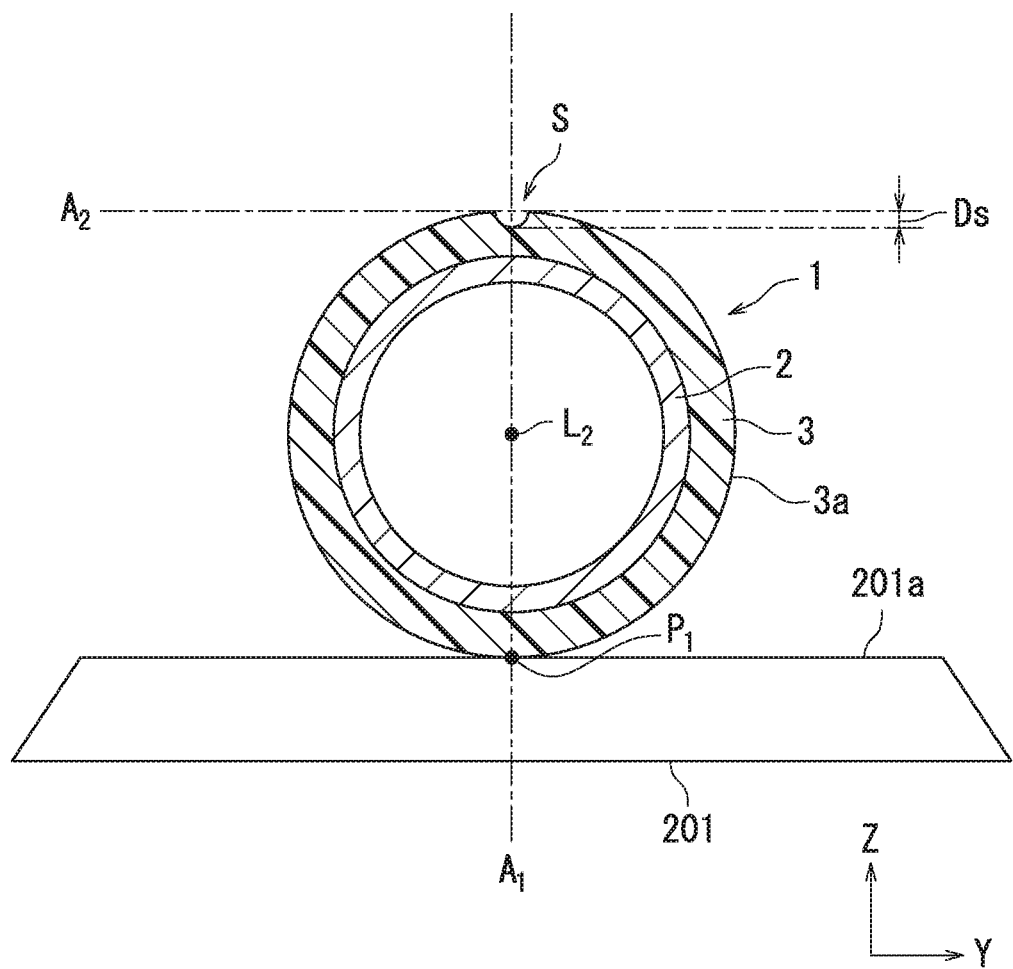
FIG. 8 is a diagram illustrating a scratch created on a surface of a photosensitive layer.

The following describes the scratch S with reference to FIG. 8 in addition to FIGS. 5 to 7. FIG. 8 illustrates the scratch S created on the surface 3a of the photosensitive layer 3. The thus created scratch S had a depth in a direction perpendicular both to the upper surface 201a of the fixture 201 and to the tangent $A_2$. The scratch S followed a line $L_3$ illustrated in FIG. 7. The line $L_3$ included a plurality of the contact points $P_2$. The line $L_3$ was parallel with the upper surface 201a of the fixture 201 and with the central axis $L_2$ of the photosensitive member 1. The line $L_3$ was perpendicular to the central axis $A_1$ of the scratching stylus 203.

(Fourth Step)

In the fourth step, the scratch depth was measured, which is a greatest value of a depth Ds of the scratch S. Specifically, the photosensitive member 1 was removed from the fixture 201. A three-dimensional interference microscope ("WYKO NT-1100", product of Bruker Corporation) was used to observe the scratch S created on the photosensitive layer 3 of the photosensitive member 1 at a magnification of 5× to measure the depth Ds of the scratch S. The depth Ds of the scratch S was defined as a distance between the tangent $A_2$ and a bottom of the scratch S. The greatest value of the measured values of the depth Ds of the scratch S was taken to be the scratch depth. Tables 1 and 2 show the scratch depth measured as described above.

[Measurement of Vickers Hardness]

With respect to each of the photosensitive members (A-1) to (A-19) and (B-1) to (B-10) obtained as described above, the Vickers hardness of the photosensitive layer (single-layer photosensitive layer) of the photosensitive member was measured. The Vickers hardness of the photosensitive layer was measured by a method in accordance with Japanese Industrial Standard (JIS) Z2244. The Vickers hardness was measured using a hardness tester ("MICRO VICKERS HARDNESS TESTER model DMH-1", product of Matsuzawa Co., Ltd). The Vickers hardness was measured under the following conditions: a temperature of 23° C., a diamond indenter load (test force) of 10 gf, a time to reach the test force of 5 seconds, a diamond indenter approach speed of 2 mm/second, and a test force retention time of 1 second. Tables 1 and 2 show the Vickers hardness measured as described above.

[Evaluation of Anti-Fogging Performance]

With respect to each of the photosensitive members (A-1) to (A-19) and (B-1) to (B-10) obtained as described above, anti-fogging performance was evaluated in an image formed using the photosensitive member. An image forming apparatus (modified version of "MONOCHROME PRINTER FS-1300D", product of KYOCERA Document Solutions Inc.) was used as an evaluation apparatus. The image forming apparatus adopts a direct transfer process, a contact development process, and a cleaner-less process. In the image forming apparatus, a development section cleans toner remaining on a photosensitive member. A charger of the image forming apparatus is a charging roller. "KYOCERA Document Solutions-brand paper VM-A4" sold by KYOCERA Document Solutions Inc. (A4 size) was used. A one-component developer (test sample) was used in the evaluation using the evaluation apparatus.

The evaluation apparatus was used to print an image 1 on 12,000 successive sheets of the paper under conditions of a photosensitive member rotational speed of 168 mm/second and a charge potential of +600 V. The image 1 had a coverage of 1%. Subsequently, a blank image was printed on a sheet of the paper. The printing was performed under environmental conditions of a temperature of 32.5° C. and a relative humidity of 80%. An image density of each of three sections in the printed blank image was measured using a reflectance densitometer ("RD914", product of X-Rite Inc.). A sum of the image densities of the three sections of the blank image was divided by the number of the measured sections. Thus, a number average image density of the blank image was obtained. A value calculated by subtracting an image density of the paper that was not subjected to printing from the number average image density of the blank image was taken to be a fogging density. The thus obtained fogging density was rated in accordance with the following rating standard. Anti-fogging performance of the photosensitive member was evaluated as good if the image fogging density thereof was rated as A or B. Anti-fogging performance of the photosensitive member was evaluated as poor if the image fogging density thereof was rated as C. The fogging density (FD) and the rating results are shown in Tables 1 and 2.
(Rating Standard for Anti-fogging Performance)
A: Fogging density≤0.010
B: 0.010<Fogging density≤0.020
C: Fogging density>0.020 from 0.10 μm to 0.42 μm. The Vickers hardness of the photosensitive layer of each of the photosensitive members (A-1) to (A-19) was from 19.0 HV to 22.6 HV. Anti-fogging performance of each of the photosensitive members (A-1) to (A-19) was evaluated as good with a rating "A".

TABLE 1

| | Photosensitive member | Binder resin | | Electron transport material Type | Scratch depth (μm) | Vickers hardness (HV) | Anti-fogging Performance | |
| --- | --- | --- | --- | --- | --- | --- | --- | --- |
| | | Type | Molecular weight | | | | FD | Rating |
| Example 1 | A-1 | R-1 | 33,000 | ETM3-1 | 0.18 | 19.6 | 0.003 | A |
| Example 2 | A-2 | R-2 | 34,200 | ETM3-1 | 0.13 | 20.2 | 0.003 | A |
| Example 3 | A-3 | R-3 | 31,300 | ETM3-1 | 0.19 | 19.8 | 0.003 | A |
| Example 4 | A-4 | R-4 | 32,000 | ETM3-1 | 0.15 | 20.2 | 0.003 | A |
| Example 5 | A-5 | R-5 | 34,000 | ETM3-1 | 0.11 | 21.0 | 0.002 | A |
| Example 6 | A-6 | R-6 | 33,100 | ETM3-1 | 0.16 | 20.8 | 0.003 | A |
| Example 7 | A-7 | R-7 | 32,700 | ETM3-1 | 0.40 | 19.0 | 0.008 | A |
| Example 8 | A-8 | R-1 | 33,000 | ETM4-1 | 0.17 | 20.8 | 0.003 | A |
| Example 9 | A-9 | R-2 | 34,200 | ETM4-1 | 0.14 | 21.9 | 0.003 | A |
| Example 10 | A-10 | R-3 | 31,300 | ETM4-1 | 0.18 | 21.7 | 0.003 | A |
| Example 11 | A-11 | R-4 | 32,000 | ETM4-1 | 0.16 | 21.5 | 0.003 | A |
| Example 12 | A-12 | R-5 | 34,000 | ETM4-1 | 0.10 | 22.2 | 0.002 | A |
| Example 13 | A-13 | R-6 | 33,100 | ETM4-1 | 0.13 | 22.2 | 0.003 | A |
| Example 14 | A-14 | R-7 | 32,700 | ETM4-1 | 0.42 | 19.8 | 0.009 | A |
| Example 15 | A-15 | R-1 | 33,000 | ETM1-1 | 0.16 | 21.6 | 0.003 | A |
| Example 16 | A-16 | R-1 | 33,000 | ETM2-1 | 0.15 | 22.3 | 0.003 | A |
| Example 17 | A-17 | R-1 | 33,000 | ETM5-1 | 0.15 | 22.6 | 0.003 | A |
| Example 18 | A-18 | R-8 | 32,400 | ETM3-1 | 0.23 | 19.0 | 0.004 | A |
| Example 19 | A-19 | R-9 | 31,200 | ETM3-1 | 0.13 | 19.9 | 0.002 | A |

TABLE 2

| | Photosensitive member | Binder resin | | Electron transport material Type | Scratch depth (μm) | Vickers hardness (HV) | Anti-fogging Performance | |
| --- | --- | --- | --- | --- | --- | --- | --- | --- |
| | | Type | Molecular weight | | | | FD | Rating |
| Comparative Example 1 | B-1 | R-12 | 31,000 | ETM1-1 | 0.88 | 12.2 | 0.032 | C |
| Comparative Example 2 | B-2 | R-13 | 32,500 | ETM1-1 | 0.91 | 13.5 | 0.035 | C |
| Comparative Example 3 | B-3 | R-14 | 33,000 | ETM1-1 | 0.70 | 18.1 | 0.029 | C |
| Comparative Example 4 | B-4 | R-15 | 34,500 | ETM1-1 | 0.89 | 17.9 | 0.044 | C |
| Comparative Example 5 | B-5 | R-14 | 33,000 | ETM6-1 | 1.20 | 13.2 | 0.092 | C |
| Comparative Example 6 | B-6 | R-14 | 33,000 | ETM7-1 | 1.30 | 14.0 | 0.098 | C |
| Comparative Example 7 | B-7 | R-3 | 33,000 | ETM6-1 | 0.44 | 15.0 | 0.025 | C |
| Comparative Example 8 | B-8 | R-3 | 33,000 | ETM7-1 | 0.46 | 14.8 | 0.030 | C |
| Comparative Example 9 | B-9 | R-16 | 34,200 | ETM1-1 | 0.52 | 18.2 | 0.024 | C |
| Comparative Example 10 | B-10 | R-17 | 32,600 | ETM1-1 | 0.56 | 17.5 | 0.027 | C |

As shown in Table 1, each of the photosensitive members (A-1) to (A-19) contained one of the polyarylate resins (R-1) to (R-9) each having repeating units encompassed by general formula (1). Each of the photosensitive members (A-1) to (A-19) contained one of the electron transport materials (ETM1-1) to (ETM5-1), which are each encompassed by general formula (ETM1), general formula (ETM2), general formula (ETM3), general formula (ETM4), or general formula (ETM5). The scratch depth of the photosensitive layer of each of the photosensitive members (A-1) to (A-19) was As shown in Table 2, each of the photosensitive members (B-1) to (B-6), (B-9), and (B-10) contained one of the resins (R-12) to (R-17), which are not encompassed by general formula (1). Each of the photosensitive members (B-5) to (B-8) contained one of the electron transport materials (ETM6-1) and (ETM7-1), which are not encompassed by any of general formula (ETM1), general formula (ETM2), general formula (ETM3), general formula (ETM4), and general formula (ETM5). The scratch depth of the photosensitive layer of each of the photosensitive members (B-1)

to (B-6), (B-9), and (B-10) was greater than 0.50 μm. The Vickers hardness of the photosensitive layer of each of the photosensitive members (B-1), (B-2), and (B-5) to (B-8) was less than 17.0 HV. Anti-fogging performance of each of the photosensitive members (B-1) to (B-10) was evaluated as poor with a rating "C".

As evident from Tables 1 and 2, the photosensitive members (A-1) to (A-19) showed higher anti-fogging performance than the photosensitive members (B-1) to (B-10). The image forming apparatus showed higher anti-fogging performance when the image forming apparatus included any of the photosensitive members (A-1) to (A-19) than when the image forming apparatus included any of the photosensitive members (B-1) to (B-10).

INDUSTRIAL APPLICABILITY

The electrophotographic photosensitive member according to the present invention is applicable to image forming apparatuses such as multifunction peripherals.

The invention claimed is:

1. An electrophotographic photosensitive member comprising a conductive substrate and a photosensitive layer, wherein
   the photosensitive layer is a single-layer photosensitive layer and contains a charge generating material, a hole transport material, an electron transport material, and a binder resin,
   the binder resin includes a polyarylate resin,
   the polyarylate resin is represented by general formula (1) shown below,
   the electron transport material is represented by general formula (ETM1), general formula (ETM2), general formula (ETM3), general formula (ETM4), or general formula (ETM5) shown below,
   a scratch resistant depth of the photosensitive layer is no greater than 0.50 μm, and
   a Vickers hardness of the photosensitive layer is at least 17.0 HV,

[Formula 1]

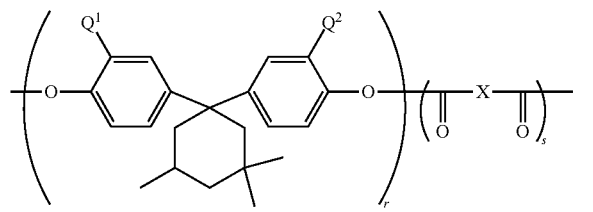

(1)

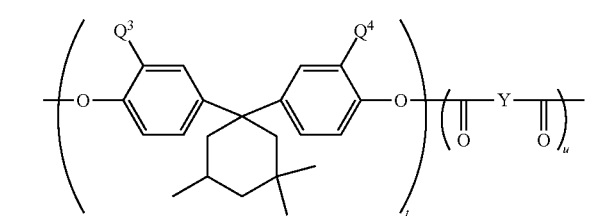

where in general formula (1),
Q$^1$, Q$^2$, Q$^3$, and Q$^4$ each represent, independently of one another, a methyl group or a hydrogen atom, r, s, t, and u each represent, independently of one another, a number greater than or equal to 15 and less than or equal to 35, r+s+t+u=100, r+t=s+u, X and Y each represent, independently of one another, a divalent group represented by chemical formula (2A), chemical formula (2B), chemical formula (2C), or chemical formula (2D) shown below, and X and Y are different from each other,

[Formula 2]

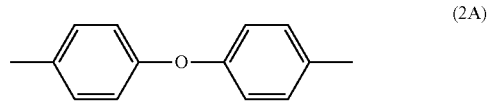

(2A)

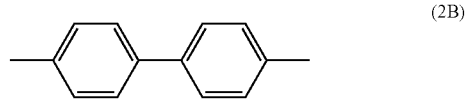

(2B)

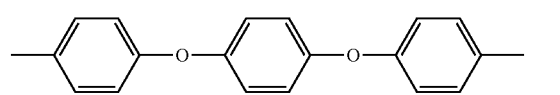

(2C)

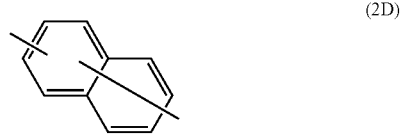

(2D)

[Formula 3]

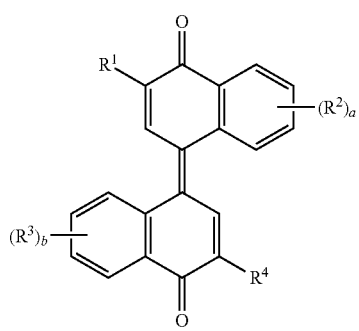

(ETM1)

[Formula 4]

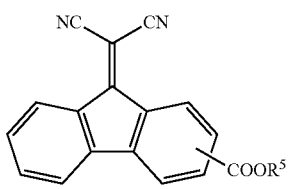

(ETM2)

[Formula 5]

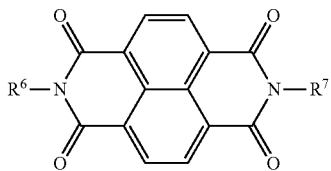

(ETM3)

[Formula 6]

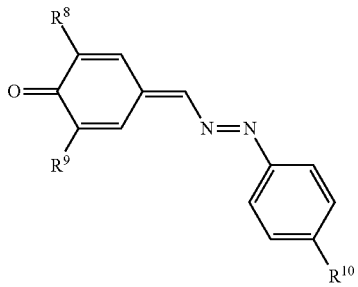

(ETM4)

[Formula 7]

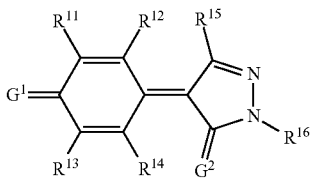

(ETM5)

in general formula (ETM1),

R$^1$ and R$^4$ each represent, independently of one another, a hydrogen atom or an alkyl group having a carbon number of at least 1 and no greater than 6, R$^2$ and R$^3$ each represent, independently of one another, an alkyl group having a carbon number of at least 1 and no greater than 6, a and b each represent, independently of one another, an integer of at least 0 and no greater than 4, when a represents an integer of at least 2 and no greater than 4, chemical groups R$^2$ may be the same as or different from one another, and when b represents an integer of at least 2 and no greater than 4, chemical groups R$^3$ may be the same as or different from one another, in general formula (ETM2), R$^5$ represents a hydrogen atom or an alkyl group having a carbon number of at least 1 and no greater than 6 and optionally having a halogen atom, in general formula (ETM3), R$^6$ and R$^7$ each represent, independently of one another, a hydrogen atom or an aryl group having a carbon number of at least 6 and no greater than 14 and optionally having an alkyl group having a carbon number of at least 1 and no greater than 3, in general formula (ETM4), R$^8$ and R$^9$ each represent, independently of one another, a hydrogen atom or an alkyl group having a carbon number of at least 1 and no greater than 6, and R$^{10}$ represents a halogen atom or a hydrogen atom, and in general formula (ETM5), R$^{11}$, R$^{12}$, R$^{13}$, R$^{14}$, and R$^{15}$ each represent, independently of one another, a hydrogen atom or an alkyl group having a carbon number of at least 1 and no greater than 6, R$^{16}$ represents a hydrogen atom or an aryl group having a carbon number of at least 6 and no greater than 14 and optionally having a halogen atom, and G$^1$ and G$^2$ each represent, independently of one another, an oxygen atom or a sulfur atom.

2. The electrophotographic photosensitive member according to claim 1, wherein in general formula (1), X and Y each represent, independently of one another, the divalent group represented by chemical formula (2A), chemical formula (2B), or chemical formula (2D).

3. The electrophotographic photosensitive member according to claim 2, wherein in general formula (1), X is the divalent group represented by chemical formula (2D), and Y is the divalent group represented by chemical formula (2A) or chemical formula (2B).

4. The electrophotographic photosensitive member according to claim 1, wherein in general formula (1), Q$^1$, Q$^2$, Q$^3$, and Q$^4$ each represent a methyl group.

5. The electrophotographic photosensitive member according to claim 1, wherein in general formula (1), r, s, t, and u each represent, independently of one another, a number greater than or equal to 20 and less than or equal to 30.

6. The electrophotographic photosensitive member according to claim 1, wherein the polyarylate resin is represented by chemical formula (R-1), chemical formula (R-2), chemical formula (R-3), chemical formula (R-4), chemical formula (R-5), chemical formula (R-6), chemical formula (R-7), chemical formula (R-8), or chemical formula (R-9) shown below

[Formula 8]

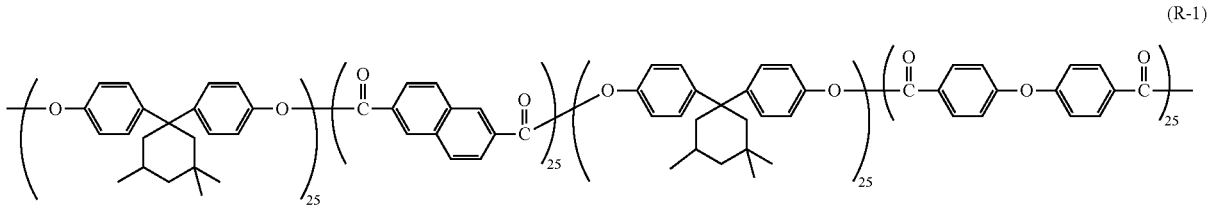

(R-1)

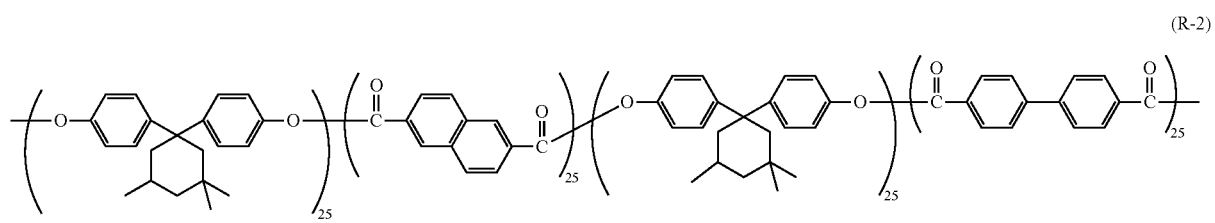
(R-2)
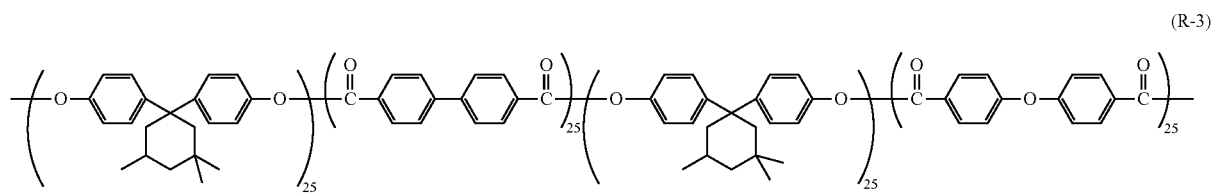
(R-3)
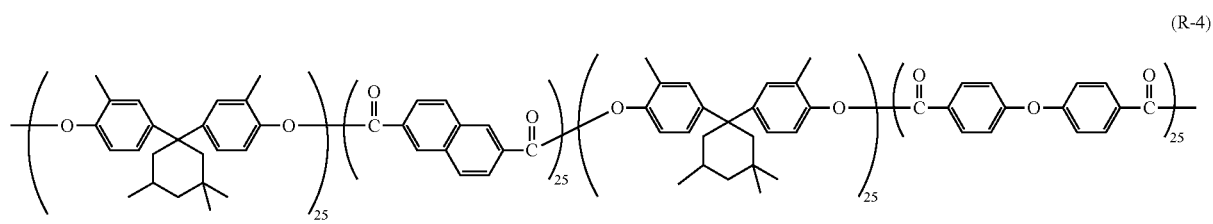
(R-4)
[Formula 9]
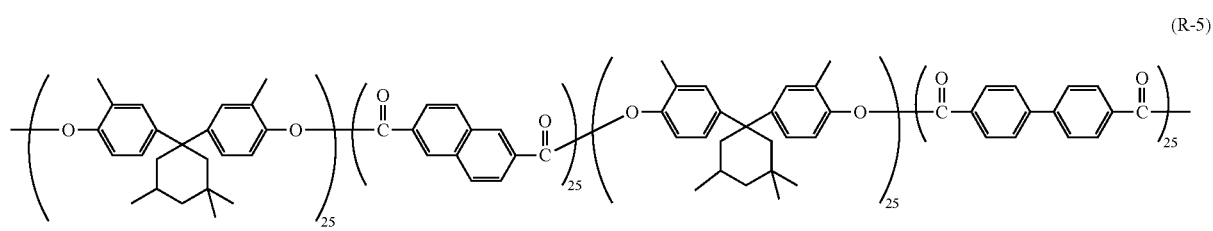
(R-5)
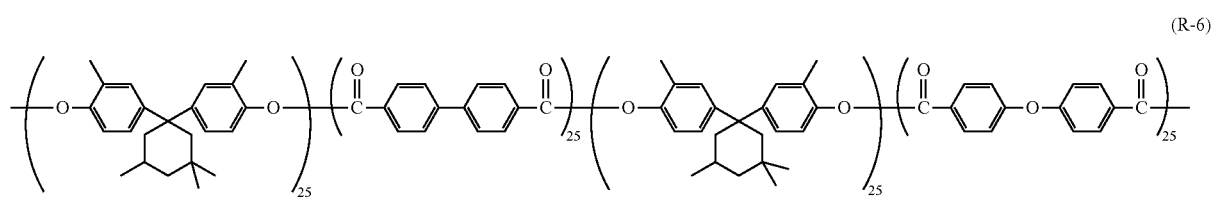
(R-6)
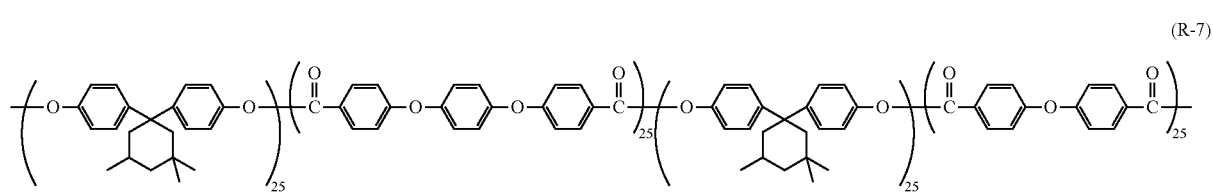
(R-7)
[Formula 10]
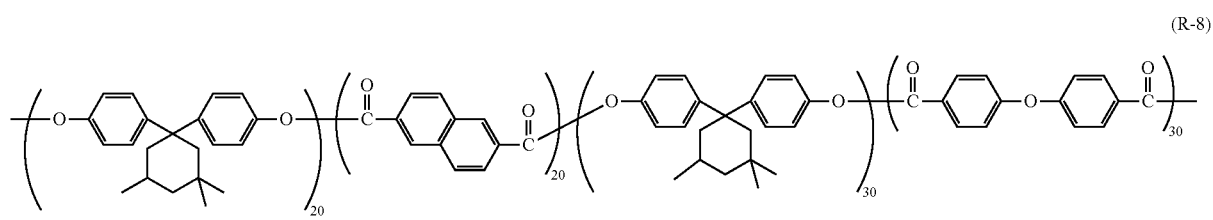
(R-8)

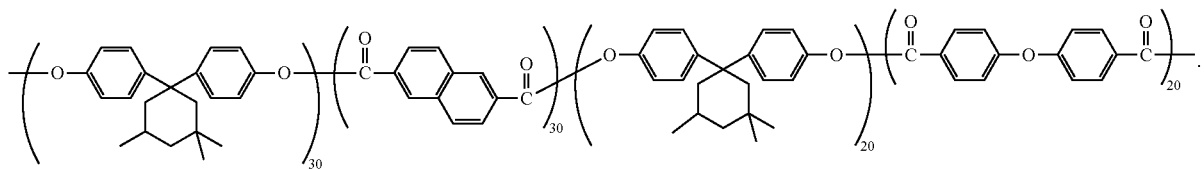

7. The electrophotographic photosensitive member according to claim 1, wherein
the electron transport material is represented by general formula (ETM1), general formula (ETM2), or general formula (ETM5).

8. The electrophotographic photosensitive member according to claim 1, wherein
in general formula (ETM1),
$R^1$ and $R^4$ each represent, independently of one another, an alkyl group having a carbon number of at least 1 and no greater than 6, and
a and b each represent 0,
in general formula (ETM2), $R^5$ represents an alkyl group having a carbon number of at least 1 and no greater than 6 and optionally having a halogen atom,
in general formula (ETM3), $R^6$ and $R^7$ each represent, independently of one another, an aryl group having a carbon number of at least 6 and no greater than 14 and optionally having an alkyl group having a carbon number of at least 1 and no greater than 3,
in general formula (ETM4), $R^8$ and $R^9$ each represent, independently of one another, an alkyl group having a carbon number of at least 1 and no greater than 6, and
$R^{10}$ represents a halogen atom, and
in general formula (ETM5),
$R^{11}$, $R^{13}$, and $R^{15}$ each represent, independently of one another, an alkyl group having a carbon number of at least 1 and no greater than 6,
$R^{12}$ and $R^{14}$ each represent a hydrogen atom,
$R^{16}$ represents an aryl group having a carbon number of at least 6 and no greater than 14 and optionally having a halogen atom, and
$G^1$ and $G^2$ each represent an oxygen atom.

9. The electrophotographic photosensitive member according to claim 8, wherein
the electron transport material is represented by chemical formula (ETM1-1), chemical formula (ETM2-1), chemical formula (ETM3-1), chemical formula (ETM4-1), or chemical formula (ETM5-1) shown below

[Formula 11]

(ETM1-1)

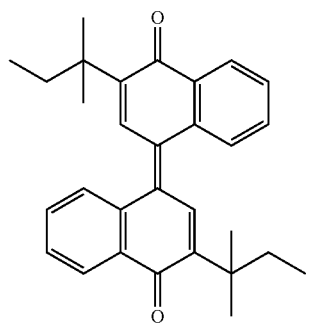

[Formula 12]

(ETM2-1)

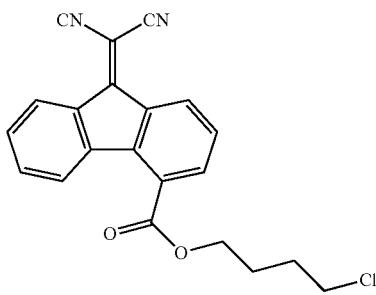

[Formula 13]

(ETM3-1)

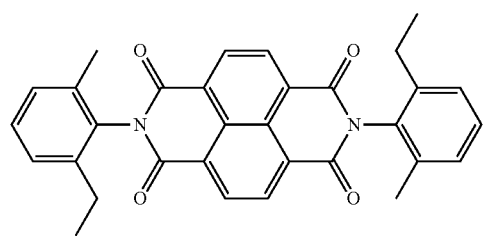

[Formula 14]

(ETM4-1)

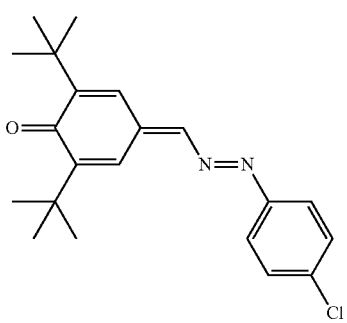

[Formula 15]

(ETM5-1)

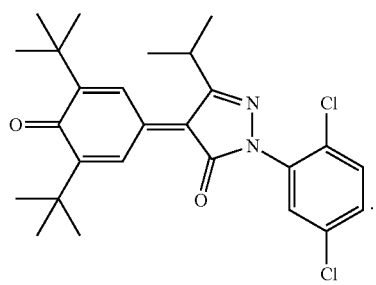

10. The electrophotographic photosensitive member according to claim 1, wherein
the hole transport material includes a compound represented by general formula (HTM1) shown below,

[Formula 16]

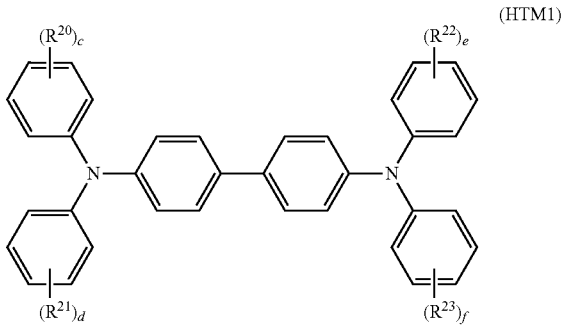

(HTM1)

where in general formula (HTM1),
$R^{20}$, $R^{21}$, $R^{22}$, and $R^{23}$ each represent, independently of one another, an alkyl group having a carbon number of at least 1 and no greater than 6,
c, d, e, and f each represent, independently of one another, an integer of at least 0 and no greater than 5,
when c represents an integer of at least 2 and no greater than 5, chemical groups $R^{20}$ may be the same as or different from one another,
when d represents an integer of at least 2 and no greater than 5, chemical groups $R^{21}$ may be the same as or different from one another,
when e represents an integer of at least 2 and no greater than 5, chemical groups $R^{22}$ may be the same as or different from one another, and
when f represents an integer of at least 2 and no greater than 5, chemical groups $R^{23}$ may be the same as or different from one another.

11. The electrophotographic photosensitive member according to claim 10, wherein
the hole transport material includes a compound represented by chemical formula (HTM1-1) shown below

[Formula 17]

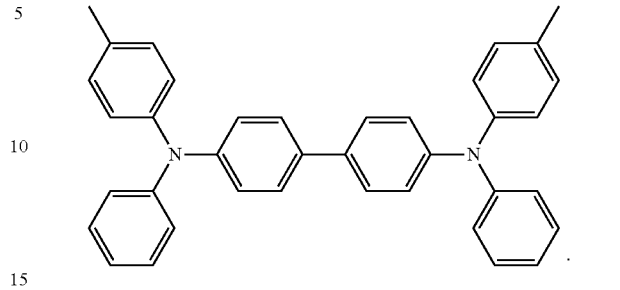

(HTM1-1)

12. The electrophotographic photosensitive member according to claim 1, wherein
the charge generating material includes X-form metal-free phthalocyanine.

13. A process cartridge comprising the electrophotographic photosensitive member according to claim 1.

14. An image forming apparatus comprising:
an image bearing member;
a charger configured to charge a surface of the image bearing member;
a light exposure section configured to expose the charged surface of the image bearing member to light to form an electrostatic latent image on the surface of the image bearing member;
a development section configured to develop the electrostatic latent image into a toner image; and
a transfer section configured to transfer the toner image from the image bearing member to a transfer target, wherein
the image bearing member is the electrophotographic photosensitive member according to claim 1,
the charger has a positive charging polarity, and
the transfer section transfers the toner image from the image bearing member to the transfer target while bringing the transfer target into contact with the surface of the image bearing member.

15. The image forming apparatus according to claim 14, wherein
the transfer target is a recording medium.

* * * * *